(12) United States Patent
Okada et al.

(10) Patent No.: US 7,709,583 B2
(45) Date of Patent: May 4, 2010

(54) SULFUR-CONTAINING CYCLIC OLEFIN RESIN AND ITS PRODUCTION METHOD

(75) Inventors: Takashi Okada, Kuwana (JP);
Toshihide Yamamoto, Yokkaichi (JP);
Hiroshi Yamakawa, Yokkaichi (JP)

(73) Assignee: Tosoh Corporation, Shunan-shi (JP)

( * ) Notice: Subject to any disclaimer, the term of this patent is extended or adjusted under 35 U.S.C. 154(b) by 155 days.

(21) Appl. No.: 11/914,806

(22) PCT Filed: May 15, 2006

(86) PCT No.: PCT/JP2006/309681
§ 371 (c)(1), (2), (4) Date: Nov. 19, 2007

(87) PCT Pub. No.: WO2006/126415
PCT Pub. Date: Nov. 30, 2006

(65) Prior Publication Data
US 2009/0069503 A1    Mar. 12, 2009

(30) Foreign Application Priority Data

| May 24, 2005 | (JP) | ............................. 2005-150639 |
| May 24, 2005 | (JP) | ............................. 2005-150640 |
| Jun. 2, 2005 | (JP) | ............................. 2005-162287 |
| Mar. 15, 2006 | (JP) | ............................. 2006-071438 |

(51) Int. Cl.
*C08G 75/00* (2006.01)

(52) U.S. Cl. .................................... 525/535; 525/327.2

(58) Field of Classification Search ................. 523/106; 525/327.2, 535; 526/256; 549/1, 6, 11, 43, 549/49
See application file for complete search history.

(56) References Cited

FOREIGN PATENT DOCUMENTS

| JP | A-60-026024 | 2/1985 |
| JP | A-61-292601 | 12/1986 |
| JP | A-01-132625 | 5/1989 |
| JP | A-04-063807 | 2/1992 |
| JP | 5-155987 A | 6/1993 |
| JP | B-06-005323 | 1/1994 |
| JP | A-09-508649 | 9/1997 |
| JP | A-11-060706 | 3/1999 |
| JP | A-11-505880 | 5/1999 |
| JP | 3050196 | 3/2000 |
| JP | 3087421 | 7/2000 |
| JP | 3534127 | 3/2004 |

OTHER PUBLICATIONS

Polyfile, Sep. number, p. 36-43 (2004).
Nikkei Electronics, p. 79-85 (Sep. 13, 2004).

*Primary Examiner*—Randy Gulakowski
*Assistant Examiner*—Kyle Baumstein
(74) *Attorney, Agent, or Firm*—Sughrue Mion, PLLC

(57) ABSTRACT

A sulfur-containing cyclic olefin resin comprising a unit represented by the following general formula (1) and having a weight average molecular weight of from 1,000 to 1,000,000.

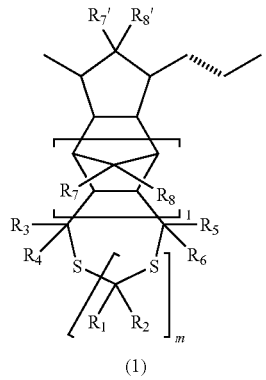

(1)

(Here, $R_1$ to $R_6$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms or a heterocyclic compound, further $R_3$ to $R_6$ may be a halogen atom, $R_3$ and $R_4$, and $R_5$ and $R_6$ may form a ring containing carbon, oxygen, sulfur or nitrogen, $R_7$ and $R_{8'}$ each independently represents a hydrogen atom or a methyl group, . . . represents a single bond or a double bond, and l and m each is 0 or 1.)

14 Claims, No Drawings

SULFUR-CONTAINING CYCLIC OLEFIN RESIN AND ITS PRODUCTION METHOD

TECHNICAL FIELD

The present invention relates to a novel sulfur-containing cyclic olefin resin having high transparency and high refractive index and being expected to utilization to optical materials such as various plastic lenses represented by a condensing lens, prism sheets, antireflective films, transparent coating materials such as an optical fiber coating material, optical films and the like, a novel sulfur-containing cyclic compound useful as its raw material, and its production method.

BACKGROUND ART

In recent years, a cyclic olefin resin is noted as a transparent heat-resistant resin used in optical materials (for example, see Non-Patent Document 1), and for example, cyclic olefin resins obtained by subjecting a tetracyclodecene compound or a norbornene compound to metathesis polymerization and hydrogenating the resulting polymer (for example, see Patent Documents 1 to 4), addition polymers of ethylene and a norbornene compound, or ethylene and a cyclodecene compound (for example, see Patent Document 5), and addition polymers of a norbornene compound (for example, see Patent Documents 6 to 9) are proposed.

Polymers of the norbornene compound have excellent characteristics as a transparent material for optical applications as being excellent in transparency, heat resistance and moldability and having high Abbe number.

On the other hand, in recent years, materials having high refractive index are demanded according to the tread of lightweight and size reduction of mobile devices. However, the polymers of the norbornene compound have the problem that refractive index is low.

As a method of achieving high refractive index of a transparent heat-resistant resin, a method of introducing an aromatic ring and a sulfur atom in a molecular structure is known, and as a material having an aromatic ring introduced therein, a material having a fluorene skeleton introduced therein is proposed (for example, see Patent Document 10 or Non-Patent Document 2). Further, a thiourethane resin having a sulfur atom introduced therein is proposed (for example, see Patent Document 11).

Patent Document 1: JP 3050196
Patent Document 2: JP-A-60-026024
Patent Document 3: JP-A-01-132625
Patent Document 4: JP 3087421
Patent Document 5: JP-A-61-292601
Patent Document 6: JP-A-04-063807
Patent Document 7: JP 3534127
Patent Document 8: JP-A-09-508649
Patent Document 9: JP-A-11-505880
Patent Document 10: JP-A-11-060706
Patent Document 11: JP-B-06-005323
Non-Patent Document 1: Polyfile, September number, p. 36-43 (2004)
Non-Patent Document 2: NIKKEI ELECTRONICS, p. 79-85 (2004.9.13)

DISCLOSURE OF THE INVENTION

Problems that the Invention is to Solve

However, the material having a fluorene skeleton introduced therein proposed in Patent Document 10 or Non-Patent Document 2 has the problem that the refractive index is high as 1.6 or higher, whereas the Abbe number is low. Further, the thiourethane resin having a sulfur atom introduced therein proposed in Patent Document 11 had the problem that the refractive index is high as 1.6 or higher and the Abbe number is high as 40 or higher, but the heat resistance is low as about 100° C.

Accordingly, the present invention solves the above-described problems and provides a novel sulfur-containing cyclic olefin resin having good heat resistance and useful as a resin for optical application of high transparency and high refractive index, a novel sulfur-containing cyclic compound useful as its raw material, and its production method.

Means for Solving the Problems

As a result of keen investigations to solve the above-described problems, the present inventors have found that a resin having a specific structure has good heat resistance and is useful as a resin for optical application of high transparency and high refractive index, and reached to complete the present invention.

That is, the present invention relates to a sulfur-containing cyclic olefin resin, characterized by comprising a unit represented by the following general formula (1) and having a weight average molecular weight of from 1,000 to 1,000,000, and its production method.

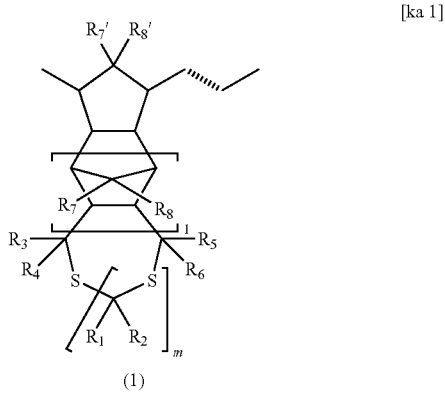

[ka 1]

(1)

(Here, $R_1$ to $R_6$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms or a heterocyclic compound, further $R_3$ to $R_6$ may be a halogen atom, $R_3$ and $R_4$, and $R_5$ and $R_6$ may form a ring containing carbon, oxygen, sulfur or nitrogen, $R_7$, $R_{7'}$, $R_8$ and $R_{8'}$ each independently represents a hydrogen atom or a methyl group, . . . represents a single bond or a double bond, and l and m each is 0 or 1.)

In particular, it relates to a sulfur-containing cyclic olefin resin, characterized by comprising a unit represented by the following general formula (2) and having a weight average molecular weight of from 1,000 to 1,000,000,

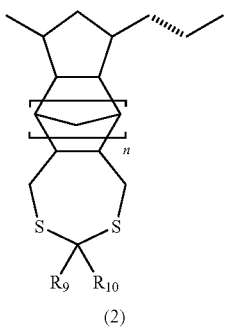

(2)

(Here, $R_9$ and $R_{10}$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms or a heterocyclic compound, . . . represents a single bond or a double bond, and n is 0 or 1.), or a sulfur-containing cyclic olefin resin, characterized by comprising a unit represented by the following general formula (3) and having a weight average molecular weight of from 1,000 to 1,000,000, and its production method.

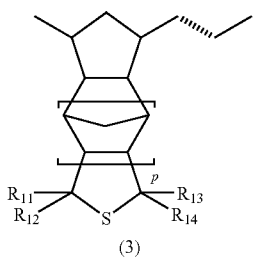

(3)

(Here, $R_{11}$ to $R_{14}$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms, a heterocyclic compound or a halogen group, $R_{11}$ and $R_{12}$, and $R_{13}$ and $R_{14}$ may form a ring containing carbon, oxygen, sulfur or nitrogen, . . . represents a single bond or a double bond, and p is 0 or 1.)

ADVANTAGE OF THE INVENTION

The sulfur-containing cyclic olefin resin of the present invention has high transparency and high refractive index, and is useful as a raw material of various plastic lenses, prim sheets, and the like.

BEST MODE FOR CARRYING OUT THE INVENTION

The present invention is described in detail below.

The sulfur-containing cyclic olefin resin of the present invention comprises a unit represented by the above general formula (1) and has a weight average molecular weight of from 1,000 to 1,000,000. The weight average molecular weight used herein can be measured with gel permeation chromatography.

Here, $R_1$ to $R_6$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms or a heterocyclic compound, further $R_3$ to $R_6$ may be a halogen atom, $R_3$ and $R_4$, and $R_5$ and $R_6$ may form a ring containing carbon, oxygen, sulfur or nitrogen, $R_7$, $R_{7'}$, $R_8$ and $R_{8'}$, each independently represents a hydrogen atom or a methyl group, . . . represents a single bond or a double bond, and l and m each is 0 or 1. As $R_1$ to $R_6$, for example, a hydrogen atom; an alkyl group such as a methyl group, an ethyl group, a propyl group, an isopropyl group, a butyl group, an octyl group or a dodecyl group; an aralkyl group such as a benzyl group; an aromatic group such as a phenyl group, a tolyl group or a naphthyl group; an alkoxy group such as a methoxy group or an ethoxy group; a heterocyclic compound group such as a thienyl group or pyridyl group; and a cyano group can be exemplified. Further, as $R_3$ to $R_6$, a halogen group such as fluorine, chlorine, bromine or iodine can be exemplified. Further, in the case that $R_1$ to $R_6$ are other than those, a resin obtained is poor in heat resistance and transparency. Further, in the case that the weight average molecular weight is less than 1,000, a resin becomes very brittle. On the other hand, in the case that the weight average molecular weight exceeds 1,000,000, viscosity when melting and dissolving becomes very high, so that handling properties are poor.

As the sulfur-containing cyclic olefin resin of the present invention, it is particularly preferable to be a sulfur-containing cyclic olefin resin comprising the unit represented by the above general formula (2) corresponding to a unit that in the above general formula (1), $R_3$ to $R_8$, $R_{7'}$ and $R_{8'}$ are a hydrogen atom, and m is 1.

Here, $R_9$ and $R_{10}$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms or a heterocyclic compound, and n is 0 or 1. As $R_9$ to $R_{10}$ for example, a hydrogen atom; an alkyl group such as a methyl group, an ethyl group, a propyl group, an isopropyl group, a butyl group, an octyl group or a dodecyl group; an aralkyl group such as a benzyl group; an aromatic group such as a phenyl group, a tolyl group or a naphthyl group; an alkoxy group such as a methoxy group or an ethoxy group; a heterocyclic compound group such as a thienyl group or pyridyl group; and a cyano group can be exemplified. It is particularly preferable to be a sulfur-containing cyclic olefin resin comprising a unit that in the above general formula (2), $R_9$ and $R_{10}$ are a hydrogen atom, and n is 0.

Further, as the sulfur-containing cyclic olefin resin of the present invention, it is particularly preferable to be a sulfur-containing cyclic olefin resin comprising the unit represented by the above general formula (3) corresponding to a unit that in the above general formula (1), $R_7$, $R_8$, $R_{7'}$ and $R_{8'}$ are a hydrogen atom, and m is 0.

Here, $R_{11}$ to $R_{14}$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms, a heterocyclic compound or a halogen group, $R_{11}$ and $R_{12}$, and $R_{13}$ and $R_{14}$ may form a ring containing carbon, oxygen, sulfur or nitrogen, and p is 0 or 1. As $R_{11}$ to $R_{14}$, for example, a hydrogen atom; an alkyl group such as a methyl group, an ethyl group, a propyl group, an isopropyl group, a butyl group, an octyl group or a dodecyl group; an aralkyl group such as a benzyl group; an aromatic group such as a phenyl group, a tolyl group or a naphthyl group; an alkoxy group such as a methoxy group or an ethoxy group; a heterocyclic compound group such as a thienyl group or pyridyl group; a cyano group; and a halogen group such as fluorine, chlorine, bromine or iodine can be exemplified. It is particularly preferable to be a sulfur-containing cyclic olefin resin comprising a unit that in the above general formula (3), $R_{11}$ to $R_{14}$ each is a hydrogen atom, and p is 0.

As a production method of the sulfur-containing cyclic olefin resin of the present invention, any production method may be used so far as production of the sulfur-containing cyclic olefin resin is possible, and for example, it can be produced by subjecting a sulfur-containing cyclic compound represented by the following general formula (4) to metathesis polymerization. Further, hydrogenation may be conducted after metathesis polymerization.

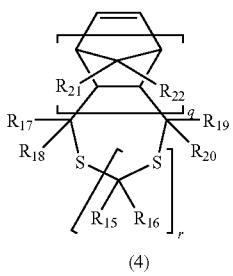

[ka 4]

(4)

(Here, $R_{15}$ to $R_{20}$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms or a heterocyclic compound, further $R_{17}$ to $R_{20}$ may be a halogen atom, $R_{17}$ and $R_{18}$, and $R_{19}$ and $R_{20}$ may form a ring containing carbon, oxygen, sulfur or nitrogen, $R_{21}$ and $R_{22}$ each independently represents a hydrogen atom or a methyl group, q is 1 or 2, and r is 0 or 1.)

As $R_{15}$ to $R_{20}$, for example, a hydrogen atom; an alkyl group such as a methyl group, an ethyl group, a propyl group, an isopropyl group, a butyl group, an octyl group or a dodecyl group; an aralkyl group such as a benzyl group; an aromatic group such as a phenyl group, a tolyl group or a naphthyl group; an alkoxy group such as a methoxy group or an ethoxy group; a heterocyclic compound group such as a thienyl group or pyridyl group; and a cyano group can be exemplified. Further, as $R_{17}$ to $R_{20}$, a halogen atom such as fluorine, chlorine, bromine and iodine can be exemplified.

Further, in producing the sulfur-containing cyclic polyolefin resin represented by the above general formula (2), it is preferable that a novel sulfur-containing cyclic compound represented by the following general formula (5) corresponding to a compound that in the sulfur-containing cyclic compound represented by the general formula (4), $R_{17}$ to $R_{22}$ are a halogen atom, and r is 1 is subjected to metathesis polymerization. Further, hydrogenation may be conducted after metathesis polymerization. The sulfur-containing cyclic compound represented by the general formula (5) is a novel compound structurally characterized by having a ring structure containing sulfur.

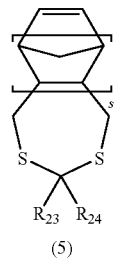

[ka 5]

(5)

(In the formula, $R_{23}$ and $R_{24}$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms or a heterocyclic compound, and s is 1 or 2.)

As $R_{23}$ and $R_{24}$, for example, a hydrogen atom; an alkyl group such as a methyl group, an ethyl group, a propyl group, an isopropyl group, a butyl group, an octyl group or a dodecyl group; an aralkyl group such as a benzyl group; an aromatic group such as a phenyl group, a tolyl group or a naphthyl group; a cyano group; an alkoxy group such as a methoxy group or an ethoxy group; and a heterocyclic compound group such as a thienyl group or pyridyl group can be exemplified.

As the sulfur-containing cyclic compound represented by the general formula (5), for example, 1,3-dithiotricyclo-[5,4,0,1$^{6,9}$]-7-dodecene, 2-methyl-1,3-di-thiotricyclo-[5,4,0,1$^{6,9}$]-7-dodecene, 2-ethyl-1,3-dithio-tricyclo-[5,4,0,1$^{6,9}$]-7-dodecene, 2-propyl-1,3-dithiotri-cyclo-[5,4,0,1$^{6,9}$]-7-dodecene, 2-isopropyl-1,3-dithiotri-cyclo-[5,4,0,1$^{6,9}$]-7-dodecene, 2-butyl-1,3-dithiotricyclo-[5,4,0,1$^{6,9}$]-7-dodecene, 2-octyl-1,3-dithiotricyclo-[5,4,0,1$^{6,9}$]-7-dodecene, 2-dodecyl-1,3-dithiotricyclo-[5,4,0,1$^{6,9}$]-7-dodecene, 2-phenyl-1,3-dithiotricyclo-[5,4,0,1$^{6,9}$]-7-dodecene, 2,2-dimethyl-1,3-dithiotricyclo-[5,4,0,1$^{6,9}$]-7-dodecene, 2,2-diethyl-1,3-dithiotricyclo-[5,4,0,1$^{6,9}$]-7-dodecene, 2,2-dipropyl-1,3-dithiotricyclo-[5,4,0,1$^{6,9}$]-7-dodecene, 2,2-dibutyl-1,3-dithiotricyclo-[5,4,0,1$^{6,9}$]-7-dodecene, 2,2-diphenyl-1,3-dithiotricyclo-[5,4,0,1$^{6,9}$]-7-dodecene, 2-methyl-2-ethyl-1,3-dithiotri-cyclo-[5,4,0,1$^{6,9}$]-7-dodecene, 2-methyl-2-propyl-1,3-dithiotricyclo-[5,4,0,1$^{6,9}$]-7-dodecene, 2-methyl-2-butyl-1,3-dithiotricyclo-[5,4,0,1$^{6,9}$]-7-dodecene, 2-methyl-2-phenyl-1,3-dithiotricyclo-[5,4,0,1$^{6,9}$]-7-dodecene, 2-ethyl-2-propyl-1,3-dithiotricyclo-[5,4,0,1$^{6,9}$]-7-dodecene, 2-ethyl-2-butyl-1,3-dithiotricyclo-[5,4,0,1$^{6,9}$]-7-dodecene, 2-ethyl-2-phenyl-1,3-dithiotricyclo-[5,4,0,1$^{6,9}$]-7-dodecene, and 2-propyl-2-phenyl-1,3-dithiotricyclo-[5,4,0,1$^{6,9}$]-7-dodecene can be exemplified.

Further, in producing the sulfur-containing cyclic polyolefin resin represented by the above general formula (3), it is preferable that a sulfur-containing cyclic compound represented by the following general formula (6) corresponding to a compound that in the sulfur-containing cyclic compound represented by the general formula (4), $R_{21}$ and $R_{22}$ are a halogen atom, and r is 0 is subjected to metathesis polymerization. Further, hydrogenation may be conducted after metathesis polymerization.

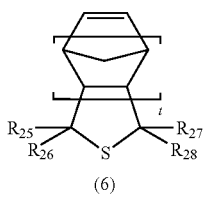

(6)

(Here, $R_{25}$ to $R_{28}$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms, a heterocyclic compound or a halogen group, $R_{25}$ and $R_{26}$, and $R_{27}$ and $R_{28}$ may form a ring containing carbon, oxygen, sulfur or nitrogen, and t is 1 or 2.)

As $R_{25}$ to $R_{28}$, for example, a hydrogen atom; an alkyl group such as a methyl group, an ethyl group, a propyl group, an isopropyl group, a butyl group, an octyl group or a dodecyl group; an aralkyl group such as a benzyl group; an aromatic group such as a phenyl group, a tolyl group or a naphthyl group; a cyano group; an alkoxy group such as a methoxy group or an ethoxy group; a heterocyclic compound group such as a thienyl group, or pyridyl group; and a halogen group such as fluorine, chlorine, bromine and iodine can be exemplified.

As the sulfur-containing cyclic compound represented by the general formula (6), for example, 2-thia-1,2-dihydroxydicyclopentadiene, 2-thia-1,3-dimethyl-1,2-dihydroxydicyclopentadiene, 2-thia-1,3-diethyl-1,2-dihydroxydicyclopentadiene, 2-thia-1,3-dipropyl-1,2-dihydroxydicyclopentadiene, 2-thia-1,3-dibutyl-1,2-dihydroxydicyclopentadiene, 2-thia-1,3-dioctyl-1,2-dihydroxydicyclopentadiene, 2-thia-1,3-didodecyl-1,2-dihydroxydicyclopentadiene, 2-thia-1,3-dimethoxy-1,2-dihydroxydicyclopentadiene, 2-thia-1,3-diethoxy-1,2-dihydroxydicyclopentadiene, 2-thia-1,3-dicyano-1,2-dihydroxydicyclopentadiene, 2-thia-1,3-di(2-thienyl)-1,2-dihydroxydicyclopentadiene, 2-thia-1,3-di(2-pyridinyl)-1,2-dihydroxydicyclopentadiene, 2-thia-1,3-di(4-pyridinyl)-1,2-dihydroxydicyclopentadiene, 2-thia-1,3-dichloro-1,2-dihydroxydicyclopentadiene, 2-thia-1,3-dibromo-1,2-dihydroxydicyclopentadiene, and 2-thia-1,3-diiodo-1,2-dihydroxydicyclopentadiene can be exemplified.

As a metathesis polymerization catalyst in subjecting the sulfur-containing cyclic compounds represented by the general formulae (4), (5) and (6) to metathesis polymerization, the conventional catalysts can be used. For example, a polymerization catalyst comprising at least one metal compound (I) selected from a ruthenium compound, a palladium compound, a rhodium compound, an iridium compound, a platinum compound, a tungsten compound, a molybdenum compound and a rhenium compound, and a metal compound (II) of Group 1, 2, 3 and 4 in the periodic table can be exemplified.

As the ruthenium compound, the palladium compound, the rhodium compound, the iridium compound, the platinum compound, the tungsten compound, the molybdenum compound and the rhenium compound that are the metal compound (I), for example, a halide, an oxyhalide, an alkoxyhalide, a carboxylate, an acetylacetonate coordination compound, an acetylacetonate coordination compound of an oxide, an acetonitrile coordination compound, a hydride complex and a carbene complex can be exemplified, and in particular, metathesis polymerization catalysts represented by the following general formulae (10) and (11) are preferably used.

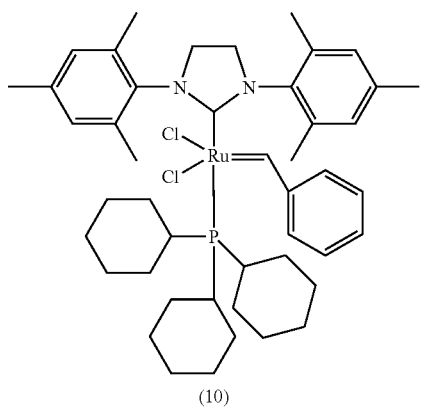

(10)

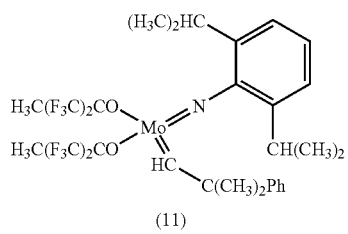

(11)

Further, a halide and an oxyhalide have high polymerization activity, and are suitable. Specifically, $WCl_6$, $WOCl_4$, $MoCl_5$, $MoOCl_3$, $ReCl_3$, $WCl_2(OC_6H_5)_4$, $MoO_2(acac)_2$, $W(OCOR)_5$ and the like can be exemplified.

Further, as the metal compounds of groups 1, 2, 3 and 4 in the periodic table that are the metal compound (II), for example, n-butyl lithium, diethyl zinc, triethyl aluminum, diethyl aluminum chloride, ethyl aluminum dichloride, diethyl aluminum hydride, trimethyl gallium, tetramethyl tin and tetraphenyl tin are exemplified, and in particular, tetramethyl tin and tetraphenyl tin are preferable.

In the case that the metal compound (I) is a carbene complex, the carbene complex alone shows sufficient activity as a metathesis polymerization catalyst. Ratio in the case that the metathesis polymerization catalyst comprises a combination of the metal compound (I) and the metal compound (II) is preferable to be metal compound (I)/metal compound (II) (molar ratio of metal atom)=1/1 to 1/30, and it is particularly preferable to use in a range of from 1/2 to 1/20. Further, as activity improver, alcohols, aldehydes, ketones and amines may be added.

In the case of the metathesis polymerization, a solvent may be used. As the solvent, for example, alkanes such as pentane, octane and nonane; cycloalkanes such as cyclohexane, cycloheptane and cyclooctane; aromatic hydrocarbons such as benzene, toluene and xylene; halogenated alkanes such as methylene chloride, dichloroethane and chloroform; halogenated aromatic hydrocarbons such as chlorobenzene and dichlorobenzene; carboxylates; cyclic ethers such as tetrahydrofuran; and linear dialkyl ethers can be exemplified.

In the case of the metathesis polymerization, it is possible to use a molecular weight modifier, and as the molecular weight modifier, an acyclic olefin compound is generally used. For example, α-olefins such as ethylene, 1-hexene and 1-heptene; vinyl sulfide compounds such as vinyl-phenyl sulfide; vinyl ethers such as vinyl-ethyl ether; and monoolefin compounds such as stilbene, 1,4-dichloro-2-butene, 1,4-diacetoxy-2-butene and 2-butene can preferably be used. Further, the molecular weight modifier can be used in two kinds or more. Use amount of the molecular weight modifier is preferably monomer charged/molecular weight modifier (molar ratio)=1/0.001 to 0.5, and it is particularly preferable to be 1/0.002 to 0.4.

As polymerization temperature in the case of the metathesis polymerization, it is preferable to be from −30° C. to 150° C., and as polymerization time, it is preferable to be from several minutes to 10 hours.

Further, in producing the sulfur-containing cyclic olefin resin of the present invention, a copolymerizable monomer that is copolymerizable with the sulfur-containing cyclic compounds represented by the above general formulae (4), (5) and (6) may be copolymerized so far as the object of the present invention is not deviated. As the copolymerizable monomer, for example, cyclobutene, cyclopentene, cyclooctene, 1,5-cyclooctadiene, 1,5,9-cyclododecatriene, bicycle[2,2,1]-2-heptene, tricycle-[5,2,1,0$^{2,6}$]-3-decene, tricyclo[5, 2, 1,0$^{2,6}$]-8-decene, tricyclo[6,2,1,0$^{1,8}$]-9-undecene, tricyclo[6,2,1,0$^{1,8}$]-4-undecene, tetracyclo[4,4,0,1$^{2,5}$,1$^{7,10}$]-3-dodecene, penta-cyclo[6,5,1,1$^{3,6}$,0$^{2,7}$,0$^{9,13}$]-4-pentadecene, pentacyclo-[6,5,1,1$^{3,6}$,0$^{2,7}$,0$^{9,13}$]-11-pentadecene, pentacyclo-[6,5,1,1$^{3,6}$,0$^{2,7}$,0$^{9,14}$]-4-hexadecene and pentacyclo-[6,5,1,1$^{3,6}$,0$^{2,7}$,0$^{9,13}$]-pentadeca-4,11-diene are exemplified, and above all, cyloolefins are preferably used.

A polymer obtained just after the metathesis polymerization has a double bond in the polymer structure. This double bond can be changed to a single bond by hydrogenation. The hydrogenation can use a general hydrogenation catalyst of olefinic compounds. As the hydrogenation catalyst, for example, supporting catalysts having palladium, platinum, nickel, rhodium, ruthenium or the like supported on carbon, silica, alumina or titania; and homogeneous catalysts such as nickel naphthenate, nickel acetyl acetonate, cobalt octenate, titanocene dichloride, rhodium acetate, chlorotris(triphenylphosphine)rhodium, dichlorotris(triphenylphosphine)-ruthenium, chlorohydrocarbonyl tris(triphenylphosphine)-ruthenium and dichlorocarbonyl tris(triphenylphosphine)-ruthenium are exemplified. Further, as a co-catalyst of those catalysts, for example, alkylaluminums such as triethylaluminum; and alkyl lithiums such as n-butyl lithium may be used together.

Form of the hydrogenation catalyst is not particularly limited, and powdery form and granular form can be used without problem. The hydrogenation catalyst is preferably used in an amount of from 0.01 to 50% in weight ratio to the polymer.

As hydrogenation conditions, it is preferable that reaction pressure is from normal pressure to 300 atm, and it is particularly preferable to react under from 3 to 200 atm. As reaction temperature, 0 to 200° C. is preferable, and it is particularly preferable to be from 20 to 180° C.

A solvent in the hydrogenation is not particularly limited, and from the points of economic efficiency and workability, it is preferable to use a solvent common to a polymerization solvent in the case of the metathesis polymerization.

As other hydrogenation method, hydrogenation can easily be conducted by using a reducing agent such as p-toluenenesulfonyl hydrazide. In such a case, use amount of the reducing agent is preferably from 1 to 50 times in molar ratio to a double bond in the polymer.

Further, the degree of hydrogenation is generally 60% or more, preferably 90% or more, and more preferably 98% or more.

As the hydrogenation conditions in the case of using a reducing agent, the reaction temperature is preferably from 0 to 200° C., and it is particularly preferable to be from 20 to 180° C.

Further, a solvent in such a case is not particularly limited, and from the points of economic efficiency and workability, it is preferable to use a solvent common to a polymerization solvent in the case of the metathesis polymerization.

The sulfur-containing cyclic compound represented by the general formula (4), (5) or (6) that is the raw material of the sulfur-containing cyclic olefin resin of the present invention may be produced by any method. For example, regarding a novel sulfur-containing cyclic compound represented by the general formula (5), a) a method of producing by reacting a compound represented by the following general formula (7) and a compound selected from the group consisting of ketones, aldehydes and acetals in the presence of an acid catalyst, b) a method of producing by reacting a compound represented by the following general formula (8) and a dihalide, and c) a method of producing by Diels-Alder reaction of a compound represented by the following general formula (9) and cyclopentadiene or dicyclopnetadiene can be exemplified.

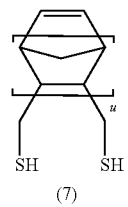

[ka 9]

(7)

(In the formula, u is 1 or 2.)

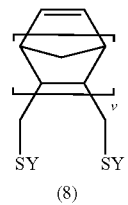

[ka 10]

(8)

(In the formula, Y is Na, K, Rb or Cs, and v is 1 or 2.)

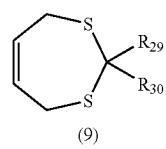

[ka 11]

(9)

(In the formula, $R_{29}$ and $R_{30}$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms or a heterocylic compound.)

One embodiment of a preferable production method of a novel sulfur-containing cyclic compound represented by the general formula (5) is specifically shown below.

a) A method of producing a novel sulfur-containing cyclic compound by reacting a compound represented by the above general formula (7) and a compound selected from the group consisting of ketones, aldehydes and acetals in the presence of an acid catalyst.

As a production method of the compound represented by the general formula (7), any production method may be used. For example, a method described in J. Am. Chem. Soc., 109, 6825-6835 (1987) is exemplified.

The above method reacts 2,3-bis(hydroxymethyl)-5-norbornene and toluenesulfonyl chloride to form a ditosylate. Next, potassium thiocyanate is reacted with the ditosylate to convert a tosyl group into a thiocyano group, and by reducing with lithium aluminum hydride, the compound represented by the general formula (7) is formed.

Proportion of 2,3-bis(hydroxymethyl)-5-norbornene and toluenesulfonyl chloride used is 2 moles or more, and preferably from 2 moles to 3 moles, of toluenesulfonyl chloride per 1 mole of 2,3-bis(hydroxymethyl)-5-norbornene. Tosylation reaction is conducted in a solvent, and as the solvent used, pyridine, triethylamine and dimethylaniline can be exemplified. Further, those solvents may be used as mixtures of two or more thereof, or may be used in combination with a hydrocarbon solvent such as toluene and xylene. Reaction temperature is generally from −78° C. to 150° C., and in particular, −20° C. to 100° C. is preferable. Reaction time is from several minutes to 96 hours, and in particular, 1 hour to 72 hours is preferable.

The ditosylate obtained is that a tosyl group is converted into a thiocyano group with potassium thiocyanate.

Proportion of ditosylate and potassium thiocyanate is 2 moles or more, and preferably from 2 to 4 moles, of potassium thiocyanate to 1 mole of ditocylate. This reaction is conducted in a solvent, and as the solvent used, dimethylacetamide, dimethylformamide, dimethyl-sulfoxide, sulfolane and N-methylpyrrolidone can be exemplified. Further, those solvents may be used as mixtures of two or more thereof, and may be used in combination with alcohols such as methanol and ethanol, or water. Reaction temperature is generally from −78° C. to 200° C., and in particular, −20° C. to 150° C. is preferable. Reaction time is from several minutes to 72 hours, and in particular, 1 hour to 48 hours is preferable.

The dithiocyano product obtained is reduced with lithium aluminum hydride to form dithiol. Proportion of the dithiocyano product and lithium aluminum hydride is that lithium aluminum hydride is used in an amount of from 1 mole to 10 moles to 1 mole of the dithiocyano product, and in particular, 2 to 4 moles is preferable. Reaction is conducted in a solvent, and as the solvent used, dimethoxyethane, diethoxyethane, diethyl ether, tetrahydrofuran and dioxane can be exemplified. Further, those solvents may be used as mixtures of two or more thereof. Reaction temperature is generally from −78° C. to 200° C., and in particular, −78° C. to 100° C. is preferable. Reaction time is from several minutes to 72 hours, and in particular, 1 hour to 48 hours is preferable.

A novel sulfur-containing cyclic compound represented by the general formula (5) can be obtained by cyclization reacting the compound represented by the general formula (7) obtained and a compound selected from the group consisting of aldehydes, ketones and acetal compounds in a solvent in the presence of an acid catalyst. As the aldehydes, for example, formaldehyde, acetaldehyde, propyl aldehyde, benzaldehyde, naphthyl aldehyde, octyl aldehyde, dodecyl aldehyde, α-formyl toluene, 2-thiophene carboaldehyde, 3-thiophene carboaldehyde, 2-pyridine carboaldehyde and 4-pyridine carboaldehyde are exemplified. As the ketones, for example, acetone, ethyl methyl ketone, acetophenone, benzophenone, fluorenone, 2-acetylthiophene, 2-acetylpyridine and 4-acetylpyridine are exemplified. As the acetals, for example, dimethoxymethane, 1,1-dimethoxyethane, 2,2-dimethoxypropane, α-dimethoxyethyl-benzene and 9,9-dimethoxyfluorene are exemplified.

As the solvent used in the case of the cyclization reaction, for example, hydrocarbons such as hexane and cyclohexane; aromatic hydrocarbons such as benzene and toluene; ethers such as diethyl ether and dioxane; alcohols such as methanol, ethanol and ethylene glycol; water; and halogenated hydrocarbons such as dichloromethane and chloroform are exemplified. The solvent may be used alone or as mixtures of two or more thereof. As the acid catalyst, for example, protonic acids such as hydrogen chloride, hydrogen bromide and sulfuric acid; Lewis acids such as trifluoroborate and aluminum chloride; and complexes such as ethers, alcohols and carboxylic acids of the Lewis acids can be exemplified. Further, as the reaction temperature, a range of from −78° C. to 200° C. is preferable, and in particular, it is preferable to be a range of from −20° C. to 150° C. As the reaction time, several minutes to 100 hours is preferable, and in particular, it is preferable to be from 1 to 48 hours.

b) A method of producing a novel sulfur-containing cyclic compound by reacting the compound represented by the above general formula (8) and a dihalide.

The compound represented by the general formula (8) is obtained by, for example, neutralizing the compound represented by the general formula (7) with an alkali metal compound.

As the alkali metal compound, for example, sodium hydroxide, potassium hydroxide, rubidium hydroxide, cesium hydroxide, sodium hydride, potassium hydride, sodium carbonate, potassium carbonate, rubidium carbonate, cesium carbonate, sodium hydrogen carbonate and potassium hydrogen carbonate are exemplified.

The neutralization reaction is conducted in a solvent that does not participate in the reaction. As the solvent, for example, hydrocarbon solvents such as n-hexane, benzene and toluene; ethers such as diethyl ether; aprotic polar solvents such as dimethylformamide, diethylacetamide, N-methyl-2-pyrrolidone, dimethyl-sulfoxide and sulfolane; and alcohols such as methanol and ethanol can be exemplified. As the reaction temperature, −78° C. to 150° C. is preferable, and it is particularly preferable that initial stage of the reaction is 50° C. or lower. As the reaction time, it is preferable to be a range of from 10 minutes to 10 hours.

The novel sulfur-containing cyclic compound represented by the general formula (5) can be obtained by cyclization reacting the compound represented by the general formula (8) and a dihalide. As the dihalide, for example, dichloromethane, 1,1-dichloroethane, 1,1-dichloropropane, 2,2-dichloropropane, α,α-dichlorotoluene, dichloroacetonitrile, 1,1-dichloro-3,3-dimethylbutane, α,α-dichloroethylbenzene, 2-dichloromethylthiophene, 2-dichloromethylpyridine, 4-dichloromethylpyridine, dibromo-methane, 1,1-dibromoethane, 1,1-dibromopropane, 2,2-dibromopropane, α,α-dibromotoluene, dibromoacetonitrile, 1,1-dibromo-3,3-dimethylbutane, α,α-dibromoethylbenzene, 9,9-dibromofluorene, 2-dibromomethylthiophene, 2-dibromo-methylpyridine and 4-dibromomethylpyridine can be exemplified.

The cyclization reaction can be conducted in a solvent. As the solvent, for example, hydrocarbons such as hexane and cyclohexane; aromatic hydrocarbons such as benzene and toluene; ethers such as diethyl ether and dioxane; alcohols such as methanol, ethanol and ethylene glycol; and water are exemplified. As the reaction temperature, a range of from −78° C. to 200° C. is preferable, and it is particularly preferable to be a range of from −20° C. to 150° C. As the reaction time, several minutes to 100 hours is preferable, and it is particularly preferable to be from 1 to 20 hours.

c) A method of producing a novel sulfur-containing cyclic compound by Diels-Alder reaction of the compound represented by the above general formula (9) and cyclopentadiene or dicyclopentadiene.

The compound represented by the above general formula (9) may be one obtained by any production method, and for example, a method as described in Organic Preparations and Procedures International, 10, 133-136 (1978) is exemplified.

This reaction forms the compound represented by the general formula (9) by synthesizing a diisothiuronium salt from cis-1,4-dichloro-2-butene and thiourea, decomposing this salt with a potassium hydroxide aqueous solution to generate an alkali metal salt of a dithiol, and then reacting with a dihalide.

The reaction of cis-1,4-dichloro-2-butene and thiourea is conducted in an organic solvent. In this case, cis-1,4-dichloro-2-butene/thiourea (molar ratio)=1/1 to 1/4 is preferable, and it is particularly preferable to be 1/1.9 to 1/2.1 is preferable. Further, as an organic solvent in the case of the reaction, for example, alcohols such as methanol, ethanol, propanol, butanol, ethylene glycol and triethyleneglycol; and aprotic polar solvents such as dimethylformamide, dimethylacetamide, N-methyl-2-pyrrolidone, dimethylsufoxide and sulfolane can be exemplified. In particular, methanol and ethanol are preferable. As the use amount of the organic solvent, 50 to 500% by weight to the sum of cis-1,4-dichloro-2-butene and thiourea is preferable, and it is particularly preferable to be from 100 to 300% by weight. The reaction temperature is preferable to be from 0° C. to 150° C., and it is particularly preferable to be from 50° C. to 130° C. As the reaction time, 10 minutes to 24 hours is preferable, and it is particularly preferable to conduct for from 30 minutes to 12 hours. Further, the reaction of cis-1,4-dichloro-2-butene and thiourea can be conducted in the absence of a catalyst/in the presence of an acid catalyst. As the acid catalyst, for example, it is preferable to be protonic acids such as sulfuric acid, hydrochloric acid, hydrobromic acid and acetic acid.

A diisothiuronium salt can be recovered by cooling the reaction liquid obtained to −78° C. to 80° C., and preferably −20° C. to 50° C.

The diisothiuronium salt is decomposed with an alkaline aqueous solution or amine, thereby 1,4-dimercapto-2-butenedithiol and a metal salt of the dithiol can be synthesized. As the alkaline compound, for example, sodium hydroxide, potassium hydroxide, rubidium hydroxide, cesium hydroxide, sodium carbonate, potassium carbonate, rubidium carbonate, cesium carbonate and sodium hydrogen carbonate are exemplified. As the amine, for example, ammonia, methylamine, trimethylamine, triethylamine, morpholine and diazabicyclo-[2,2,2]-octane are exemplified, and above all, decomposition by an alkaline aqueous solution using sodium hydroxide or potassium hydroxide is particularly preferable.

Further, diisothironium salt/alkaline compound or amine (molar ratio)=1/2 to 1/15 is preferable, and it is particularly preferable to be 1/4 to 1/10. As the temperature in this case, 0° C. to 150° C. is preferable, and it is particularly preferable to be from 50° C. to 130° C.

The compound represented by the general formula (9) can be obtained by reacting the alkali metal salt of 1,4-dimercapto-2-butene and a dihalide. As the dihalide, for example, dichloromethane, 1,1-dichloroethane, 1,1-dichloropropane, 2,2-dichloropropane, α,α-dichlorotoluene, dichloroacetonitrile, 1,1-dichloro-3,3-dimethylbutane, α,α-dichloro ethylbenzene, 2-dichloromethylthiophene, 2-dichloromethylpyridine, 4-dichloromethylpyridine, dibromo-methane, 1,1-dibromoethane, 1,1-dibromopropane, 2,2-dibromopropane, α,α-dibromotoluene, dibromoacetonitrile, 1,1-dibromo-3,3-dimethylbutane, α,α-dibromoethylbenzene, 9,9-dibromo fluorene, 2-dibromomethylthiophene, 2-dibromo-methylpyridine and 4-dibromomethylpyridine are exemplified. As the organic solvent, for example, alcohols such as methanol, ethanol, propanol, butanol, ethylene glycol and triethylene glycol; and aprotic polar solvents such as dimethylformamide, dimethylacetamide, N-methyl-2-pyrrolidone, dimethylsufoxide and sulfolane are exemplified.

In such a case, it is preferable to be alkali metal salt of 1,4-dimercapto-2-butene/dihalide (molar ratio)=1/0.1 to 1/2, and it is particularly preferable to be 1/0.9 to 1.1. Further, it is preferable that the use amount of the organic solvent is from 100% by weight to 2,000% by weight to the sum of the alkali metal salt of 1,4-dimercapto-2-butene and the dihalide, and it is particularly preferable to be from 200% by weight to 1,000% by weight. As the reaction temperature, it is preferable to be from −78° C. to 150° C., and it is particularly preferable to be from −20° C. to 130° C.

Further, when the diisothiuronium salt is decomposed with an amine or the alkali metal salt of 1,4-dimercapto-2-butene is neutralized with an acid, 1,4-dimercapto-2-butene is obtained. The compound represented by the above general formula (9) can be synthesized by reacting the 1,4-mercapto-2-butene and a compound selected from the group consisting of aldehydes, ketones and acetals in an organic solvent using an acid catalyst.

As the aldehydes, for example, formaldehyde, acetaldehyde, propyl aldehyde, benzaldehyde, naphthyl aldehyde, octyl aldehyde, dodecyl aldehyde, α-formyl toluene, 2-thiophene carboaldehyde, 3-thiophene carboaldehyde, 2-pyridine carboaldehyde and 4-pyridine carboaldehyde are exemplified. As the ketones, for example, acetone, methyl ethyl ketone, acetophenone, benzophenone, fluorenone, 2-acetylthiophene, 2-acetylpyridine and 4-acetylpyridine are exemplified. As the acetals, for example, dimethoxymethane, 1,1-dimethoxyethane, 2,2-dimethoxypropane, α-dimethoxyethyl-benzene and 9,9-dimethoxyfluorene are exemplified.

As the solvent used in the case of the cyclization reaction, for example, hydrocarbons such as hexane and cyclohexane; aromatic hydrocarbons such as benzene and toluene; ethers such as diethyl ether and dioxane; alcohols such as methanol, ethanol and ethylene glycol; water; and halogenated hydrocarbons such as dichloromethane and chloroform are exemplified. The solvent may be used alone or as mixtures of two or more thereof. As the acid catalyst, for example, protonic acids such as hydrogen chloride, hydrogen bromide and sulfuric acid; Lewis acids such as trifluoroborate and aluminum chloride; and complexes such as ethers, alcohols and carboxylic acids of the Lewis acids can be exemplified. Further, as the reaction temperature, a range of from −78° C. to 200° C. is preferable, and it is particularly preferable to be a range of from −20° C. to 150° C. As the reaction time, several minutes to 100 hours is preferable, and it is particularly preferable to be from 1 to 48 hours.

The novel sulfur-containing cyclic compound represented by the general formula (5) can be produced by Diels-Alder reaction of the compound represented by the above general formula (9) and cyclopentadiene or dicyclopentadiene. The Diels-Alder reaction can be carried out by mixing and heating the compound represented by the general formula (9) and cyclopentadiene or dicyclopentadiene in a solvent or in the absence of a solvent. As the solvent, for example, hydrocarbon solvents such as n-hexane, benzene and toluene can be exemplified. Further, cyclopentadiene or dicyclo-pentadiene acts as a solvent. Therefore, considering economic efficiency, it is preferable to react in the absence of a solvent.

Here, it is preferable to be compound represented by the general formula (9)/cyclopentadiene or dicyclo-pentadiene (molar ratio)=1/0.01 to 1/5, and it is particularly preferable to be 1/0.1 to 1/2.0. Further, in the case of carrying out the Diels-Alder reaction, the reaction may be carried out in the absence of a catalyst, or a catalyst for promoting the reaction may be used. In the case of using the catalyst, compound represented by the general formula (9)/catalyst (molar ratio) =1/0.001 to 1/1 is preferable. As the catalyst, for example, Lewis acids such as aluminum chloride, aluminum bromide, tin tetrachloride, titanium tetrachloride, zinc chloride and trifluoro borate are preferable. Further, as the reaction temperature, a range of from −10 to 300° C. is preferable, and it is particularly preferable to be from 20 to 230° C. As the reaction time, several minutes to 100 hours is preferable, 30 minutes to 50 hours is particularly preferable, and it is further preferable to be from 1 to 20 hours.

Further, the sulfur-containing cyclic compound represented by the above general formula (6) can be synthesized by, for example, Diels-Alder reaction of cyclopentadiene or dicyclopentadiene and 2,5-dihydrothiophene derivatives. The Diels-Alder reaction can be carried out by mixing and heating cyclopentadiene and 2,5-dihydrothiophene derivatives in a solvent or in the absence of a solvent. As the solvent, for example, hydrocarbon solvents such as n-hexane, benzene and toluene can be exemplified. Further, cyclopentadiene or dicyclopentadiene is liquid and acts as a solvent. Therefore, considering economic efficiency, it is preferable to react in the absence of a solvent.

Here, it is preferable to be 2,5-dihydrothiophene derivative/cyclopentadiene or dicyclopentadiene (molar ratio)=1/ 0.01 to 1/5, and it is particularly preferable to be 1/0.1 to 1/2. Further, in carrying out the Diels-Alder reaction, the reaction may be carried out in the absence of a catalyst, or a catalyst for promoting the reaction may be used. In the case of using the catalyst, 1,2-dihydrothiophene derivative/catalyst (molar ratio)=1/0.001 to 1/1 is preferable. As the catalyst, for example, Lewis acids such as aluminum chloride, aluminum bromide, tin tetrachloride, titanium tetrachloride, zinc chloride and trifluoro borate are preferable. Further, as the reaction temperature, a range of from −10 to 300° C. is preferable, and it is particularly preferable to be from 20 to 230° C. As the reaction time, several minutes to 100 hours is preferable, from 30 minutes to 50 hours is particularly preferable, and it is further preferable to be from 1 to 20 hours.

Further, as the synthesis of a compound corresponding to the sulfur-containing cyclic compound represented by the general formula (6) wherein t is 1 and $R_{25}$ to $R_{28}$ are a hydrogen atom, the method described in J. Org. Chem., 30, 2560-2564 (1965) is exemplified.

The above-mentioned method forms dimesylate by reacting 2,3-bis(hydroxylmethyl)-5-norbornene and methane-sulfonyl chloride. Next, sodium sulfide is reacted with the dimesylate to synthesize a compound corresponding to the sulfur-containing cyclic compound represented by the general formula (6) wherein t is 1 and $R_{25}$ to $R_{28}$ are a hydrogen atom.

The proportion of 2,3-bis(hydroxymethyl)-5-norbornene and methanesulfonyl chloride is that methanesulfonyl chloride is 2 moles or more, and preferably from 2 moles to 3 moles, per 1 mole of 2,3-bis(hydroxymethyl)-5-norbornene. The mesylation reaction is conducted in a solvent, and as the solvent, pyridine, triethylamine and dimethylaniline can be exemplified. Further, those solvents may be used as mixtures of two or more thereof, and hydrocarbon solvents such as toluene and xylene may be used in combination. The reaction temperature is generally from −78° C. to 150° C., and −20° C. to 100° C. is particularly preferable. The reaction time is from several minutes to 96 hours, and from 1 hour to 72 hours is particularly preferable.

The dimesylate obtained is reacted with sodium sulfide, and thereby a compound corresponding to the sulfur-containing cyclic compound represented by the general formula (6) wherein t is 1 and $R_{25}$ to $R_{28}$ are a hydrogen atom can be synthesized.

The proportion of dimesylate and sodium sulfide is that sodium sulfide is 1 mole or more, and preferably from 2 to 4 moles, per 1 mole of dimesylate. This reaction is conducted in a solvent, and the solvent can exemplify methanol, ethanol, dimethylacetamide, dimethylformamide, dimethylsulfoxide, sulfolane and N-methylpyrrolidone. Further, those solvents may be used as mixtures of two or more thereof, and water may be used in combination. The reaction temperature is generally from −78° C. to 200° C., and −20° C. to 150° C. is particularly preferable. The reaction time is from several minutes to 72 hours, and 1 hour to 48 hours is particularly preferable.

The sulfur-containing cyclic olefin resin of the present invention has high transparency, and can be used as transparent coating materials such as a antireflective film and an optical fiber coating material, optical materials such as an optical film, various films, sheets, lenses, substrates and the like. Above all, because of having high refractive index, it can be used as plastic lenses represented by a condensing lens, prism sheets, and the like.

The present invention is described by the Examples below, but those Examples do not limit the present invention in any way.

Measurement of Weight Average Molecular Weight

Using gel permeation chromatography (GPC) (a product of Tosoh Corporation, trade name: HLC8020GPC), it was measured as a standard polystyrene conversion value from an elution curve measured at 40° C. using chloroform as a solvent.

Measurement of Infrared Absorption Spectrum (IR)

Using an infrared absorption measurement device (a product of Hitachi, Ltd., trade name: Infrared Spectrophotometer 270-30), IR spectrum was measured with KBr method.

Measurement of NMR Spectrum

Using a nuclear magnetic resonance spectrum measurement device (a product of JEOL, trade name: GSX270WB), it was measured using Chloroform-d as a heavy solvent.

Measurement of GC-MS

Using gas chromatography mass analyzer (a product of Hewlett-Packard Company, trade name: Mass analyzer 5971 Series), measurement was made using a capillary column having an outer diameter of 0.25 mm and a length of 30 m (a product of GL Science Inc., trade name: DB-1) as a column.

Ray Transmission

Measured according to JIS K7105

Refractive Index (nd)

Using Abbe's refractometer (a product of Atago Co., Ltd., trade name: DR-M2), it was measured with d ray. Refractive index ($n_D$) of sulfur-containing cyclic compound Using liquid refractometer (a product of Atago Co., Ltd., trade name: RX-5000α (digital refractometer)), it was measured as a toluene solution.

Synthesis Example 1

Synthesis of 5-norbornene-2,3-dicarboxylic acid isopropyl ester 27.1 g (0.2 mol) of dicyclopentadiene and 80.4 g (0.4 mol) of diisopropylfumarate were charged in a 200 ml autoclave, and after sufficiently replacing with nitrogen, reaction was conducted at 170° C. for 5 hours. The reaction liquid was distilled under reduced pressure of 0.4 kPa to obtain 88 g of a fraction of 124-126° C. It was confirmed by $^1$H-NMR spectrum and GC-MS that this fraction is 5-norbornene-2,3-dicarboxylic acid diisopropyl ester. Yield: 83%.

Measurement result by 270 MHz $^1$H-NMR δ(CDCl$_3$): 1.2 (12H), 1.4-1.6 (2H), 2.6 (1H), 3.1-3.4 (3H), 5.0 (2H), 6.1-6.3 (2H)

EI-MS: 266 (M)

Synthesis of 5-norbornene-2,3-dimethanol 25.8 g (0.68 mol) of lithium aluminum hydride was charged in a glass-made 1,000 ml four-necked flask equipped with a stirrer, a reflux condenser, a thermometer and a nitrogen inlet tube, and after sufficiently replacing with nitrogen, 450 ml of tetrahydrofuran (hereinafter referred to as THF) was gradually added while cooling with an ice water bath. A mixture of 37.8 g (0.14 mol) of 5-norbornene-2,3-dicarboxylic acid diisopropyl ester and 50 ml of THF was added dropwise thereto such that temperature of the mixture does not exceed 10° C. After completion of the addition, reaction was conducted at a reflux temperature of THF for 5 hours. After completion of the reaction, the mixture was again cooled to 5° C. with an ice water bath, and 150 g of 3% NaOH aqueous solution was added dropwise over about 1 hour. Stirring was continued for about 30 minutes, and a precipitate was suction filtered off.

A solvent was removed by an evaporator, flowed by drying with a vacuum dryer at room temperature for 5 hours to obtain 20.4 g of a pale orange viscous liquid. This viscous liquid was 5-norbornene-2,3-dimethanol by $^1$H-NMR spectrum and GC-MS. Yield: 98%.

Measurement result by 270 MHz $^1$H-NMR δ(CDCl$_3$): 1.3 (1H), 1.6-2.0 (2H), 2.5-3.1 (5H), 3.4-3.8 (4H), 6.0-6.2 (2H)

EI-MS: 154 (M)

Synthesis of 5-norbornene-2,3-dimethanol-di-p-toluene-sulfonate 20.3 g (0.13 mol) of 5-norbornene-2,3-dimethanol and 90 ml of pyridine were charged in a glass-made 500 ml four-necked flask equipped with a stirrer, a reflux condenser, a thermometer and a nitrogen inlet tube, and the mixture was cooled to 5° C. with an ice water bath. 59.4 g (0.31 mol) of p-toluenesulfonyl chloride was added to this solution over 20 minutes. When stirring was continued for about 20 minutes, the mixture was solidified. The whole reactor was placed in a refrigerator adjusted to 4° C. for 72 hours.

The reaction product was added to 300 ml of 6% HCl aqueous solution, followed by stirring at room temperature for 2 hours. A white slurry solution formed was suction filtered. A white solid obtained was washed with 200 ml of methanol two times, and dried in a vacuum dryer at 50° C. for 2 hours to obtain 53.2 g of a white solid. From $^1$H-NMR spectrum, this solid was 5-norbornene-2,3-dimethanol-di-p-toluenesulfonate. Yield: 87%.

Measurement result by 270 MHz $^1$H-NMR δ(CDCl$_3$): 1.2 (1H), 1.3-1.4 (2H), 1.9 (1H), 2.4 (6H), 2.6 (1H), 2.8 (1H), 3.5-4.0 (4H), 5.8 (1H), 6.1 (1H), 7.3 (4H), 7.7 (4H)

Synthesis of 5-norbornene-2,3-dimethylthiocyanate 147 g (0.62 mol) of potassium thiocyanate, 236 ml of dimethylformamide (hereinafter referred to as DMF) and 53 g (0.11 mol) of 5-norbornene-2,3-dimethanol-di-p-toluene-sulfonate were charged in a glass-made 1,000 ml four-necked flask equipped with a stirrer, a reflux condenser, a thermometer and a nitrogen inlet tube. After sufficiently replacing with nitrogen, temperature was elevated, and reaction was conducted at a temperature between 70° C. and 80° C. for 20 hours. The reaction liquid was allowed to stand to cool, and 200 ml of pure water was then added thereto, followed by extracting with 200 ml of diethyl ether two times. A diethyl ether layer was removed by an evaporator to obtain 23.5 g of a yellow viscous liquid. From $^1$H-NMR spectrum and GC-MS, this viscous liquid was 5-norbornene-2,3-dimethylthiocyanate. Yield: 88%.

Measurement result by 270 MHz $^1$H-NMR δ(CDCl$_3$): 1.3-1.5 (3H), 2.2 (1H), 2.7-3.2 (6H), 6.1 (1H), 6.3 (1H)

EI-MS: 236 (M)

Synthesis of 1,3-dithiotricyclo-[5,4,0,1$^{6,9}$]-7-dodecene 16.4 g (0.43 mol) of lithium aluminum hydride was charged in a glass-made 1,000 ml four-necked flask equipped with a stirrer, a reflux condenser, a thermometer and a nitrogen inlet tube. After sufficiently replacing with nitrogen, 400 ml of THF was gradually added while cooling with an ice water bath. A mixture of 23 g (0.1 mol) of 5-norbornene-2,3-dimethylthiocyanate and 100 ml of THF was added dropwise thereto over about 1 hour. After completion of the addition, reaction was conducted at room temperature for 2 hours. After completion of the reaction, the reaction mixture was again cooled to 5° C. with an ice water bath, and 25 ml of 5% sulfuric acid aqueous solution was added dropwise. Stirring was continued for about 1 hour, and a precipitate was suction filtered off. When the filtrate obtained was subjected to GC-MS analysis, 5-norbornene-2,3-dimethylthiocyanate as the raw material was not recognized, and formation of 5-norbornene-2,3-dimercaptomethyl was recognized. EI-MS: 186.

The filtrate was concentrated to 50 g by an evaporator, and 400 ml of methanol was added thereto. A solution of 22 g (0.33 mol) of 85% potassium hydroxide dissolved in 350 ml of methanol was added to the methanol solution, followed by stirring at room temperature for 30 minutes. Next, a mixture of 18.7 g (0.11 mol) of dibromomethane and 100 ml of methanol was added dropwise over about 30 minutes, followed by stirring at room temperature for 13 hours. In the reaction liquid, a salt precipitated was filtered off, and methanol was removed by an evaporator. 100 ml of chloroform was added to a slurry obtained, and after again filtering off a solid component, the filtrate was concentrated with an evaporator to obtain 16.8 g of a viscous liquid. The viscous liquid obtained was distilled under reduced pressure of 0.3 kPa to obtain 7.6 g of a fraction in a range of from 111 to 114° C. From $^1$H-NMR spectrum and GC-MS, this fraction was 1,3-dithiotricyclo-[5,4,0,1$^{6,9}$]-7-dodecene (a compound wherein $R_{23}$ and $R_{24}$ are a hydrogen atom and s is 1 in the general formula (5)).

Measurement result by 270 MHz $^1$H-NMR; δ(CDCl$_3$): 1.6 (3H), 2.2 (2H), 2.6 (2H), 2.8 (2H), 3.0 (1H), 6.1 (1H), 6.3 (1H)

EI-MS: 198 (M)

Refractive index ($n_D$): 1.597

Synthesis Example 2

Synthesis of bis(isothiuronium salt) of cis-1,4-dichloro-2-butene 120 g (1.58 mol) of thiourea and 310 ml of 95% ethanol were charged in a glass-made 1,000 ml four-necked flask equipped with a stirrer, a reflux condenser, a thermometer and a nitrogen inlet tube. After sufficiently replacing with nitrogen, temperature was elevated to 40° C., and a mixture of 90 g (0.72 mol) of cis-1,4-dichloro-2-butene and 20 ml of 95% ethanol were added dropwise over about 30 minutes (at this time, heat generation occurred). After completion of the addition, the mixture was elevated to a reflux temperature of ethanol, and reaction was conducted for 1 hour. After completion of the reaction, the system was allowed to stand to cool to room temperature, and a solid content was filtered off. This solid content was washed with 250 ml of ethanol two times, and dried in a vacuum dryer at room temperature for 8 hours to obtain 182 g of a white solid. From $^1$H-NMR spectrum and FT-IR spectrum, this white solid was a bis(isothiuronium salt) of cis-1,4-dichloro-2-butene. Yield: 90%.

Measurement result by 270 MHz $^1$H-NMR; δ(D$_2$O): 4.0 (4H), 5.9 (2H)

Measurement result of FT-IR (KBr method): 3,000-3,500 cm$^{-1}$ (NH)

Synthesis of 4,7-dihydro-1,3-dithiepin 182 g (0.66 mol) of a bis(isothiuronium salt) of cis-1,4-dichloro-2-butene and 1,900 ml of methanol were charged in a glass-made 5,000 ml four-necked flask equipped with a stirrer, a reflux condenser, a thermometer and a nitrogen inlet tube, and temperature of the mixture was cooled to 4° C. 218 g (3.31 mol) of 85% potassium hydroxide was added to this slurry solution over 1 hour, and reaction was conducted at 2 to 4° C. for 16 hours as it is. A mixture of 143 g (0.82 mol) of dibromomethane and 650 ml of methanol was added dropwise to the reaction liquid obtained over 6 hours such that the reaction temperature does not exceed 5° C. The reaction liquid was gradually returned to room temperature over one night, and stirring was continued for 60 hours as it is.

The reaction liquid obtained was filtered to remove a solid content, and methanol was removed by an evaporator, followed by drying in a vacuum dryer at room temperature for 1 hour, thereby obtaining 50.1 g of a pale yellow solid. From $^1$H-NMR spectrum and GC-MS, this pale yellow solid was 4,7-dihydro-1,3-dithiepin. Yield: 58%.

Measurement result by 270 MHz $^1$H-NMR; δ(CDCl$_3$): 3.45 (4H), 4.02 (2H), 6.00 (2H)

EI-MS: 132 (M)

Synthesis of 1,3-dithiotricyclo-[5,4,0,1$^{6,9}$]-7-dodecene 12.2 g (0.09 mol) of dicyclopentadiene and 49.1 g (0.37 mol) of 4,7-dihydro-1,3-dithiepin were charged in 200 ml autoclave, and after sufficiently replacing with nitrogen, heat stirring was continued at 170° C. for 5 hours while stirring. After completion of the reaction, temperature was lowered to 25° C., and the reaction liquid was taken out of the autoclave. The reaction liquid was a brown solution. The brown solution obtained was distilled under reduced pressure of 0.3 kPa to obtain 23.5 g of a fraction in a range of from 111 to 114° C. This fraction solidified at room temperature. From $^1$H-NMR spectrum and GC-MS, this was 1,3-dithiotricyclo-[5,4,0,1$^{6,9}$]-7-dodecene (a compound wherein $R_{23}$ and $R_{24}$ are a hydrogen atom and s is 1 in the general formula (5)). This compound was an isomer of the compound obtained in Synthesis Example 1.

Measurement result by 270 MHz $^1$H-NMR δ(CDCl$_3$): 1.2 (2H), 2.5-3.0 (8H), 4.0 (2H), 5.8-6.2 (2H)

EI-MS: 198 (M)

Refractive index ($n_D$): 1.610

Synthesis Example 3

Synthesis of 7-methyl-5-norbornene-2,3-dicarboxylic acid diisopropyl ester 32.0 g (0.4 mol) of 1-methylcyclopentadiene and 80.4 g (0.4 mol) of diisopropylfumarate were charged in 200 ml autoclave, and after sufficiently replacing with nitrogen, reaction was conducted at 170° C. for 5 hours. The reaction liquid was distilled under reduced pressure of 0.4 kPa to obtain 94 g of a fraction of from 124 to 126° C. From $^1$H-NMR spectrum and GC-MS, this fraction was confirmed to be 7-methyl-5-norbornene-2,3-dicarboxylic acid diisopropyl ester. Yield: 84%.

Measurement result by 270 MHz $^1$H-NMR δ(CDCl$_3$): 1.2 (14H), 1.4-1.6 (2H), 2.6 (1H), 3.1-3.4 (3H), 5.0 (2H), 6.1-6.3 (2H)

EI-MS: 280 (M)

Synthesis of 7-methyl-5-norbornene-2,3-dimethanol 25.8 g (0.68 mol) of lithium aluminum hydride was charged in a glass-made 1,000 ml four-necked flask equipped with a stirrer, a reflux condenser, a thermometer and a nitrogen inlet tube, and after sufficiently replacing with nitrogen, 450 ml of THF was gradually added while cooling with an ice water bath. A mixture of 39.2 g (0.14 mol) of 7-methyl-5-norbornene-2,3-dicarboxylic acid diisopropyl ester and 50 ml of THF was added dropwise thereto such that temperature of the mixture does not exceed 10° C. After completion of the addition, reaction was conducted at a reflux temperature of THF for 5 hours. After completion of the reaction, the mixture was again cooled to 5° C. with an ice water bath, and 150 g of 3% NaOH aqueous solution was added dropwise over about 1 hour. Stirring was continued for about 30 minutes, and a precipitate was suction filtered.

A solvent was removed by an evaporator, followed by drying in a vacuum dryer at room temperature for 5 hours, thereby obtaining 23.1 g of a pale orange viscous liquid. From $^1$H-NMR spectrum and GC-MS, this viscous liquid was 7-methyl-5-norbornene-2,3-dimethanol. Yield: 98%.

Measurement result by 270 MHz $^1$H-NMR δ(CDCl$_3$): 1.3 (4H), 1.6-2.0 (1H), 2.5-3.1 (5H), 3.4-3.8 (4H), 6.0-6.2 (2H)

EI-MS: 168 (M)

Synthesis of 7-methyl-5-norbornene-2,3-dimethanol-di-p-toluenesulfonate 21.8 g (0.13 mol) of 7-methyl-5-norbornene-2,3-dimethanol and 90 ml of pyridine were charged in a glass-made 500 ml four-necked flask equipped with a stirrer, a reflux condenser, a thermometer and a nitrogen inlet tube, and the inside of a system was cooled to 5° C. with an ice water bath. 59.4 g (0.31 mol) of p-toluenesulfonyl chloride was added to this solution over 20 minutes. When stirring was continued for about 20 minutes, the mixture solidified. Therefore, the whole reactor was placed in a refrigerator adjusted to 4° C. for 72 hours.

The reaction product was added to 300 ml of 6% HCl aqueous solution, followed by stirring at room temperature for 2 hours. A white slurry solution formed was suction filtered, and a white solid obtained was washed with 200 ml of methanol two times, and dried in a vacuum dryer at 50° C. for 2 hours to obtain 53.8 g of a white solid. From $^1$H-NMR spectrum, this solid was 7-methyl-5-norbornene-2,3-dimethanol-di-p-toluenesulfonate. Yield: 87%.

Measurement result by 270 MHz $^1$H-NMR $\delta$(CDCl$_3$): 1.2 (4H), 1.3-1.4 (1H), 1.9 (1H), 2.4 (6H), 2.6 (1H), 2.8 (1H), 3.5-4.0 (4H), 5.8 (1H), 6.1 (1H), 7.3 (4H), 7.7 (4H)

Synthesis of 7-methyl-5-norbornene-2,3-dimethylthio-cyanate 147 g (0.62 mol) of potassium thiocyanate, 236 ml of DMF and 53 g (0.11 mol) of 7-methyl-5-norbornene-2,3-dimethanol-di-p-toluenesulfonate were charged in a glass-made 1,000 ml four-necked flask equipped with a stirrer, a reflux condenser, a thermometer and a nitrogen inlet tube, and after sufficiently replacing with nitrogen, temperature was elevated, and reaction was conducted between 70 and 80° C. for 20 hours. After allowing to stand the reaction liquid to cool, 200 ml of pure water was added, followed by extracting with 200 ml of diethyl ether two times. Diethyl ether layer was removed with an evaporator to obtain 23.8 g of a yellow viscous liquid. From $^1$H-NMR spectrum and GC-MS, this viscous liquid was 7-methyl-5-norbornene-2,3-dimethylthiocyanate. Yield: 87%.

Measurement result by 270 MHz $^1$H-NMR $\delta$(CDCl$_3$): 1.3-1.5 (3H), 2.2 (1H), 2.7-3.2 (6H), 6.1 (1H), 6.3 (1H)
EI-MS: 250 (M)

Synthesis of 12-methyl-1,3-dithiotricyclo-[5,4,0,1$^{6,9}$]-7-dodecene 16.4 g (0.43 mol) of lithium aluminum hydride was charged in a glass-made 1,000 ml four-necked flask equipped with a stirrer, a reflux condenser, a thermometer and a nitrogen inlet tube, and after sufficiently replacing with nitrogen, 400 ml of THF was gradually added while cooling with an ice water bath. A mixture of 23 g (0.09 mol) of 7-methyl-5-norbornene-2,3-dimethylthiocyanate and 100 ml of THF was added dropwise thereto over about 1 hour. After completion of the addition, reaction was conducted at room temperature for 2 hours. After completion of the reaction, the mixture was again cooled to 5° C. with an ice water bath, and 25 ml of 5% sulfuric acid aqueous solution was added. Stirring was continued for about 1 hour, and a precipitate was suction filtered out. When the filtrate obtained was subjected to GC-MS analysis, 7-methyl-5-norbornene-2,3-dimethylthio-cyanate as the raw material was not recognized, and formation of 7-methyl-5-norbornene-2,3-dimercaptomethyl was recognized. EI-MS: 200.

The filtrate was concentrated to 50 g with an evaporator, and 400 ml of methanol was added thereto. A liquid of 22 g (0.33 mol) of 85% potassium hydroxide dissolved in 350 ml of methanol was added to this methanol solution, followed by stirring at room temperature for 30 minutes. Next, a mixture of 18.7 g (0.11 mol) of dibromomethane and 100 ml of methanol was added dropwise over about 30 minutes, followed by stirring at room temperature for 13 hours. A salt precipitated in the reaction liquid was filtered out, and methanol was removed with an evaporator. 100 ml of chloroform was added to a slurry obtained, a solid content was again filtered out, and the filtrate was concentrated with an evaporator to obtain 17.0 g of a viscous liquid. The viscous solution obtained was distilled under reduced pressure of 0.3 kPa to obtain 7.8 g of a fraction in a range of from 115 to 119° C. From $^1$H-NMR spectrum and GC-MS, this fraction was 12-methyl-1,3-dithiotricyclo-[5,4,0,1$^{6,9}$]-7-dodecene (a compound wherein $R_{15}$ to $R_{21}$ are a hydrogen atom, $R_{22}$ is a methyl group and q is 1 in the general formula (4)).

Measurement result by 270 MHz $^1$H-NMR; $\delta$(CDCl$_3$): 1.6 (5H), 2.2 (2H), 2.6 (2H), 2.8 (2H), 3.0 (1H), 6.1 (1H), 6.3 (1H)
EI-MS: 212 (M)
Refractive index ($n_D$): 1.590

Synthesis Example 4

Synthesis of 5-norbornene-2,3-dimethanol-dimethane-sulfonate 31 g of 5-norbornene-2,3-dimethanol was obtained in the same manner as in Synthesis Example 1.

140 ml of pyridine was charged in a glass-made 500 ml four-necked flask equipped with a stirrer, a reflux condenser, a thermometer and a nitrogen inlet tube, and after sufficiently replacing with nitrogen, temperature was lowered to 3° C. with an ice water bath. 50.3 g (0.44 mol) of methanesulfonyl chloride was added dropwise to this over about 1 hour. After stirring this solution for 1 hour, a mixture of 30 g (0.2 mol) of 5-norbornene-2,3-dimethanol and 125 ml of pyridine was gradually added for 5 hours such that temperature do not exceeds 5° C. The reaction mixture became a brown slurry state, and reaction was conducted for 15 hours as it was.

The reaction liquid was gradually added to 4% HCl ice aqueous solution, and a brown solid precipitated was suction filtered off. The brown solid obtained was washed with 500 ml of pure water two times, and then dried in a vacuum dryer at 50° C. for 8 hours to obtain 54.5 g of a pale brown solid.

From $^1$H-NMR spectrum, it was confirmed to be 5-norbornene-2,3-dimethanol-dimethanesulfonate. Yield: 90%.

Measurement result by 270 MHz $^1$H-NMR $\delta$(CDCl$_3$): 1.2-1.4 (2H), 2.7 (2H), 3.0 (8H), 3.9-4.1 (4H), 6.1 (2H)

Synthesis of 2-thia-1,2-dihydrodicyclopentadiene 25 g (0.08 mol) of 5-norbornene-2,3-dimethanol-dimethanesulfonate and 250 ml of methanol were charged in a glass-made 500 ml four-necked flask equipped with a stirrer, a reflux condenser, a thermometer and a nitrogen inlet tube, and after sufficiently replacing with nitrogen, 5-norbornene-2,3-dimethanol-dimethanesulfonate was dissolved under reflux with heating. An aqueous solution of 62 g (0.26 mol) of sodium sulfate-nonahydrate dissolved in 150 ml of pure water was added dropwise to this solution over about 4 hours. After completion of the addition, reaction was conducted for 2 hours as it was. After cooling, the reaction liquid was extracted with 100 ml of diethyl ether two times. The diethyl ether layer was washed with 100 ml of 10% NaOH aqueous solution one time, and after liquid separation, the diethyl ether was removed with a rotary evaporator to obtain 10.6 g of a black liquid. This liquid was distilled under reduced pressure of 0.1 kPa to obtain 3.8 g of a fraction of 59 to 60° C. From $^1$H-NMR spectrum and GC-MS, it was confirmed to be 2-thia-1,2-dihydrodicyclopentadiene (a compound wherein $R_{25}$ to $R_{28}$ are a hydrogen atom and t is 1 in the general formula (6)). Yield: 31%.

Measurement result by 270 MHz $^1$H-NMR; δ(CDCl$_3$): 1.62-1.80 (2H), 2.26-2.42 (2H), 2.60-2.82 (2H), 3.08-3.28 (2H), 6.11 (2H)

EI-MS: 152 (M)

Refractive index ($n_D$): 1.557

Synthesis Example 5

Synthesis of 5-norbornene-2,3-dimethanol 26.4 g (0.2 mol) of dicyclopentadiene and 70.4 g (0.8 mol) of cis-1,4-dihydroxy-2-butene were charged in 200 ml autoclave, and after sufficiently replacing with nitrogen, temperature was elevated to 170° C. while stirring, and stirring with heating was continued for 6 hours. After completion of the reaction, temperature was lowered to 25° C., and the reaction liquid was taken out of the autoclave. The reaction was a brown solution. The brown solution obtained was distilled under reduced pressure of 0.3 kPa to obtain 36.3 g of a fraction in a range of from 120 to 122° C. From $^1$H-NMR spectrum and GC-MS, this fraction was confirmed to be 5-norbornene-2,3-dimethanol. Yield: 59%.

Measurement result by 270 MHz $^1$H-NMR δ(CDCl$_3$): 1.4 (2H), 2.4-2.8 (4H), 3.2-4.3 (6H), 6.0 (2H)

EI-MS: 154 (M)

Synthesis of
5-norbornene-2,3-dimethanol-dimethane-sulfonate 140 ml of pyridine was charged in a glass-made 500 ml four-necked flask equipped with a stirrer, a reflux condenser, a thermometer and a nitrogen inlet tube, and after sufficiently replacing with nitrogen, pyridine solution was cooled with an ice water bath to lower temperature to 3° C. 50.3 g (0.44 mol) of methanesulfonyl chloride was added dropwise to this over about 1 hour. After stirring this solution for 1 hour, a mixture of 30 g (0.2 mol) of 5-norbornene-2,3-dimethanol and 125 mol of pyridine was gradually added for 5 hours such that the inside temperature of a mixture does not exceed 5° C. The mixture became a brown slurry state, and reaction was conducted for 15 hours as it was.

The reaction liquid was gradually added to 4% HCl ice aqueous solution, and a brown solid precipitated was suction filtered off. The brown solid obtained was washed with 500 ml of pure water two times, and then dried in a vacuum dryer at 50° C. for 8 hours to obtain 54.5 g of a pale brown solid. From $^1$H-NMR spectrum, it was confirmed to be 5-norbornene-2,3-dimethanol-dimethanesulfonate. Yield: 90%.

Measurement result by 270 MHz $^1$H-NMR δ(CDCl$_3$): 1.2-1.4 (2H), 2.7 (2H), 3.0 (8H), 3.9-4.1 (4H), 6.1 (2H)

Synthesis of 2-thia-1,2-dihydro dicyclopentadiene 25 g (0.08 mol) of 5-norbornene-2,3-dimethanol-dimethanesulfonate and 250 ml of methanol were charged in a glass-made 500 ml four-necked flask equipped with a stirrer, a reflux condenser, a thermometer and a nitrogen inlet tube, and after sufficiently replacing with nitrogen, 5-norbornene-2,3-dimethanol-dimethanesulfonate was dissolved under reflux with heating. An aqueous solution of 62 g (0.26 mol) of sodium sulfate.nonahydrate dissolved in 150 ml of pure water was added dropwise to this solution over about 4 hours. After completion of the addition, reaction was conducted for 2 hours as it was. After cooling, the reaction liquid was extracted with 100 ml of diethyl ether two times. The diethyl ether layer was washed with 100 ml of 10% NaOH aqueous solution one time, and after separation, the diethyl ether was removed with a rotary evaporator to obtain 10.6 g of a black liquid. This liquid was distilled under reduced pressure of 0.1 kPa to obtain 3.8 g of a fraction of 59 to 60° C. From $^1$H-NMR spectrum and GC-MS, it was confirmed to be 2-thia-1,2-dihydrodicyclopentadiene (a compound wherein $R_{25}$ to $R_{28}$ are a hydrogen atom and t is 1 in the general formula (6)). This compound is an isomer of the compound obtained in Synthesis Example 4. Yield: 31%.

Measurement result by 270 MHz $^1$H-NMR δ(CDCl$_3$): 1.8 (2H), 2.4 (2H), 2.7 (4H), 3.2 (2H), 6.2 (2H)

EI-MS: 152 (M)

Refractive index ($n_D$): 1.555

Example 1

100 ml Schlenk flask having a magnetic stirring bar therein was dried with a heat gun under reduced pressure, and was sufficiently replaced with nitrogen. 85 mg (0.1 mmol) of ruthenium complex represented by the above general formula (10) was placed in the flask. 45 ml of dried chloroform and 23 mg (0.17 mmol) of phenylvinyl sulfide were weighed with a syringe and placed in this Schlenk flask to prepare a metathesis polymerization catalyst solution. Next, 5.0 g (25 mmol) of 1,3-dithiotricyclo-[5,4,0,1$^{6,9}$]-7-dodecene obtained in Synthesis Example 1 was charged, the flask was immersed in an oil bath adjusted to 60° C., and polymerization was conducted for 4 hours.

The polymerization liquid was poured in 150 ml of acetone containing 0.1% of 2,6-di-t-butyl-4-hydroxytoluene to precipitate a polymer. After filtering out a solvent, the polymer recovered was dried in a vacuum dryer at room temperature for 8 hours to obtain 2.6 g of the polymer.

From $^1$H-NMR spectrum analysis, the polymer obtained was confirmed to be a ring-opening metathesis polymer of 1,3-dithiotricyclo-[5,4,0,1$^{6,9}$]-7-dodecene.

Measurement result by 270 MHz $^1$H-NMR; δ(CDCl$_3$): 1.2-3.1 (10H), 3.9 (2H), 5.3 (2H)

Weight average molecular weight (Mw) of this polymer was 13,000, and 10% heat weight loss temperature was 370° C.

This polymer was dissolved in chloroform, and cast on a polyethylene terephthalate film (hereinafter referred to as PET film) to prepare a film having a thickness of 100 μm. Refractive index (nd) of this film was 1.657, and Abbe number was 20. Further, light transmittance was 88%.

Example 2

300 ml four-necked flask having a magnetic stirring bar therein was dried with a heat gun under reduced pressure, and was replaced with nitrogen. 3.5 g of a ring-opening metathesis polymer of 1,3-dithiotricyclo-[5,4,0,1$^{6,9}$]-7-dodecene obtained in Example 1 and 120 ml of 1,1,2-trichloroethane were placed in the flask, followed by stirring and dissolving at room temperature. 16.5 g (88.8 mmol) of p-toluenesulfonyl hydrazide and 11.3 g (88.8 mmol) of N,N'-dimethylcyclohexyl amine were added into this solution, and reaction was conducted at 110° C. for 4 hours. After completion of the reaction, the reaction liquid was cooled to room temperature, and poured in 300 ml of methanol to precipitate a polymer. The polymer precipitated was filtered off, and then dissolved in 100 ml of chloroform, and an insoluble content was filtered out. The filtrate was poured in 300 ml of methanol to again precipitate a polymer. After filtration, the polymer recovered was dried in a vacuum dryer at 100° C. for 5 hours to obtain 2.7 g of a polymer. From $^1$H-HMR spectrum, the polymer obtained was a hydride of a ring-opening metathesis polymer of 1,3-dithiotricyclo-[5,4,0,1$^{6,9}$]-7-dodecene.

Measurement result by 270 MHz $^1$H-NMR; $\delta$(CDCl$_3$): 1.4-3.6 (10H), 5.2-5.6 (2H)

Weight average molecular weight (Mw) of this polymer was 13,000. This polymer was pressed at 220° C. to prepare a film having a thickness of 100 μm. Refractive index (nd) of this film was 1.623, and Abbe number was 45. Further, light transmittance was 88%.

Example 3

100 ml Schlenk flask having a magnetic stirring bar therein was dried with a heat gun under reduced pressure, and was sufficiently replaced with nitrogen. 85 mg (0.1 mmol) of ruthenium complex represented by the above general formula (10) was placed in the flask. 45 ml of dried chloroform was weighed with a syringe and placed in this Schlenk flask to prepare a metathesis polymerization catalyst solution. Next, 5.0 g (25 mmol) of 1,3-dithiotricyclo-[5,4,0,1$^{6,9}$]-7-dodecene (endo isomer) obtained in Synthesis Example 2 was charged, the flask was immersed in an oil bath adjusted to 60° C., and polymerization was conducted for 4 hours.

The polymerization liquid was poured in 150 ml of acetone containing 0.1% of 2,6-di-t-butyl-4-hydroxytoluene to precipitate a polymer. After filtering out a solvent, the polymer recovered was dried in a vacuum dryer at room temperature for 8 hours to obtain 1.5 g of the polymer.

From $^1$H-NMR spectrum analysis, the polymer obtained was confirmed to be a ring-opening metathesis polymer of 1,3-dithiotricyclo-[5,4,0,1$^{6,9}$]-7-dodecene.

Measurement result by 270 MHz $^1$H-NMR; $\delta$(CDCl$_3$): 1.2-3.1 (10H), 3.9 (2H), 5.3 (2H)

Weight average molecular weight (Mw) of this polymer was 7,000, and 10% heat weight loss temperature was 370° C.

This polymer was dissolved in chloroform, and cast on a PET film to prepare a film having a thickness of 100 μM. Refractive index (nd) of this film was 1.647, and Abbe number was 22. Further, light transmittance was 88%.

Example 4

200 ml four-necked flask having a magnetic stirring bar therein was dried with a heat gun under reduced pressure, and was replaced with nitrogen. 1.5 g of a ring-opening metathesis polymer of 1,3-dithiotricyclo-[5,4,0,1$^{6,9}$]-7-dodecene obtained in Example 3 and 50 ml of 1,1,2-trichloroethane were placed in the flask, followed by stirring and dissolving at room temperature. 7.1 g (38.2 mmol) of p-toluenesulfonyl hydrazide and 4.9 g (38.2 mmol) of N,N'-dimethylcyclohexyl amine were added into this solution, and reaction was conducted at 110° C. for 4 hours. After completion of the reaction, the reaction liquid was cooled to room temperature, and poured in 150 ml of methanol to precipitate a polymer. The polymer precipitated was filtered off, and then dissolved in 50 ml of chloroform, and an insoluble content was filtered out. The filtrate was poured in 150 ml of methanol to again precipitate a polymer. After filtration, the polymer recovered was dried in a vacuum dryer at 100° C. for 5 hours to obtain 1.2 g of a polymer. From $^1$H-NMR spectrum analysis, the polymer obtained was a hydride of a ring-opening metathesis polymer of 1,3-dithiotricyclo-[5,4,0,1$^{6,9}$]-7-dodecene.

Measurement result by 270 MHz $^1$H-NMR; $\delta$(CDCl$_3$): 1.4-3.6 (10H), 5.2-5.6 (2H)

Weight average molecular weight (Mw) of this polymer was 7,000. This polymer was pressed at 220° C. to prepare a film having a thickness of 100 μm. Light transmittance of this film was 89%, refractive index (nd) was 1.601, and Abbe number was 43.

Example 5

100 ml Schlenk flask having a magnetic stirring bar therein was dried with a heat gun under reduced pressure, and was sufficiently replaced with nitrogen. 76 mg (0.1 mmol) of molybdenum complex represented by the above general formula (11) was placed in the flask. 45 ml of dried chloroform and 23 mg (0.17 mmol) of phenylvinyl sulfide were weighed with a syringe and placed in this Schlenk flask to prepare a metathesis polymerization catalyst solution. Next, 5.0 g (25 mmol) of 1,3-dithiotricyclo-[5,4,0,1$^{6,9}$]-7-dodecene obtained in Synthesis Example 1 was charged, the flask was immersed in an oil bath adjusted to 60° C., and polymerization was conducted for 4 hours.

The polymerization liquid was poured in 150 ml of acetone containing 0.1% of 2,6-di-t-butyl-4-hydroxytoluene to precipitate a polymer. After filtering out a solvent, the polymer recovered was dried in a vacuum dryer at room temperature for 8 hours to obtain 2.6 g of the polymer.

From $^1$H-NMR spectrum analysis, the polymer obtained was confirmed to be a ring-opening metathesis polymer of 1,3-dithiotricyclo-[5,4,0,1$^{6,9}$]-7-dodecene.

Measurement result by 270 MHz $^1$H-NMR; $\delta$(CDCl$_3$): 1.2-3.1 (10H), 3.9 (2H), 5.3 (2H)

Weight average molecular weight (Mw) of this polymer was 23,000, and 10% heat weight loss temperature was 370° C.

This polymer was dissolved in chloroform, and cast on a PET film to prepare a film having a thickness of 100 μm. Refractive index (nd) of this film was 1.657, and Abbe number was 20. Further, light transmittance was 88%.

Example 6

100 ml Schlenik flask having a magnetic stirring bar therein was dried with a heat gun under reduced pressure, and was sufficiently replaced with nitrogen. 85 mg (0.1 mmol) of ruthenium complex represented by the above general formula (10) was placed in the flask. 45 ml of dried chloroform and 23 mg (0.17 mmol) of phenylvinyl sulfide were weighed with a syringe and placed in this Schlenik flask to prepare a metathesis polymerization catalyst solution. Next, 5.3 g (25 mmol) of 12-methyl-1,3-dithiotricyclo-[5,4,0,1$^{6,9}$]-7-dodecene obtained in Synthesis Example 3 was charged, the flask was immersed in an oil bath adjusted to 60° C., and polymerization was conducted for 4 hours.

The polymerization liquid was poured in 150 ml of acetone containing 0.1% of 2,6-di-t-butyl-4-hydroxytoluene to precipitate a polymer. After filtering out a solvent, the polymer recovered was dried in a vacuum dryer at room temperature for 8 hours to obtain 2.7 g of the polymer.

From $^1$H-NMR spectrum analysis, the polymer obtained was confirmed to be a ring-opening metathesis polymer of 12-methyl-1,3-dithiotricyclo-[5,4,0,1$^{6,9}$]-7-dodecene.

Measurement result by 270 MHz $^1$H-NMR; $\delta$(CDCl$_3$): 1.2-3.1 (12H), 3.9 (2H), 5.3 (2H)

Weight average molecular weight (Mw) of this polymer was 14,000, and 10% heat weight loss temperature was 380° C.

This polymer was dissolved in chloroform, and cast on a PET film to prepare a film having a thickness of 100 μm. Refractive index (nd) of this film was 1.643, and Abbe number was 25. Further, light transmittance was 88%.

Example 7

50 ml Schlenk flask having a magnetic stirring bar therein was dried with a heat gun under reduced pressure, and was sufficiently replaced with nitrogen. 13.2 mg (15.5 μmol) of ruthenium complex represented by the above general formula (10) was placed in the flask. 10 ml of dried chloroform and 140.3 mg (1.03 mmol) of phenylvinyl sulfide were weighed with a syringe and placed in this Schlenk flask to prepare a metathesis polymerization catalyst solution.

On the other hand, 500 ml four-necked flask having a magnetic stirring bar therein was dried with a heat gun under reduced pressure, and was replaced with nitrogen. 23.6 g (155.3 mmol) of 2-thia-1,2-dihydrodicyclopentadiene obtained in Synthesis Example 4 and 140 ml of dried chloroform were charged in the flask under nitrogen stream, and after fitting a reflux condenser, the flask was immersed in an oil bath adjusted to 60° C. After conducting stirring for 30 minutes, the whole amount of the metathesis polymerization catalyst solution prepared was added, and polymerization was conducted at 60° C. for 4 hours. The polymerization liquid was poured in 300 ml of acetone containing 0.1% of 2,6-di-t-butyl-4-hydroxytoluene to precipitate a polymer. After filtration, the polymer recovered was dried in a vacuum dryer at room temperature for 8 hours to obtain 20.6 g of the polymer.

From $^1$H-NMR spectrum analysis, the polymer obtained was confirmed to be a ring-opening metathesis polymer of 2-thia-1,2-dihydrodicyclopentadiene.

Measurement result by 270 MHz $^1$H-NMR; δ(CDCl$_3$): 1.4-3.6 (10H), 5.2-5.6 (2H)

Weight average molecular weight (Mw) of this polymer was 72,000.

This polymer was dissolved in chloroform, and cast on a PET film to prepare a film having a thickness of 100 μm. Refractive index (nd) of this film was 1.590, and Abbe number was 41. Further, light transmittance was 89%.

Example 8

300 ml four-necked flask having a magnetic stirring bar therein was dried with a heat gun under reduced pressure, and was replaced with nitrogen. 2.7 g of a ring-opening metathesis polymer of 2-thia-1,2-dihydrodicyclopentadiene obtained in Example 7 and 120 ml of o-dichlorobenzene were charged in the flask, followed by stirring and dissolving at room temperature. 16.5 g (88.8 mmol) of p-toluenesulfonyl hydrazide and 11.3 g (88.8 mmol) of N,N'-dimethylcyclohexyl amine were added into this solution, and reaction was conducted at 110° C. for 4 hours. After completion of the reaction, the reaction liquid was cooled to room temperature, and poured in 300 ml of methanol to precipitate a polymer. The polymer precipitated was filtered off, and then dissolved in 100 ml of chloroform, and an insoluble content was filtered out. The filtrate was poured in 300 ml of methanol to again precipitate a polymer. After filtration, the polymer recovered was dried in a vacuum dryer at 100° C. for 5 hours to obtain 2.7 g of a polymer. From $^1$H-NMR spectrum analysis, the polymer obtained was a hydride of a 2-thia-1,2-dihydrodicyclopentadiene ring-opening metathesis polymer.

Measurement result by 270 MHz $^1$H-NMR; δ(CDCl$_3$): 1.4-3.6 (10H), 5.2-5.6 (2H)

Weight average molecular weight (Mw) of this polymer was 72,000.

This polymer was pressed at 220° C. to prepare a film having a thickness of 100 μm. Refractive index (nd) of this film was 1.583, and Abbe number was 46. Further, light transmittance was 89%.

Example 9

100 ml Schlenik flask having a magnetic stirring bar therein was dried with a heat gun under reduced pressure, and was sufficiently replaced with nitrogen. 21 mg (25 μmol) of ruthenium complex represented by the above general formula (10) was placed in the flask. 46 ml of dried chloroform and 34 mg (0.25 mmol) of phenylvinyl sulfide were weighed with a syringe and placed in this Schlenik flask to prepare a metathesis polymerization catalyst solution. Next, 3.8 g (25 mmol) of 2-thia-1,2-dihydrodicyclopentadiene (isomer) obtained in Synthesis Example 5 was charged, the flask was immersed in an oil bath adjusted to 60° C., and polymerization was conducted for 5 hours.

The polymerization liquid was poured in 150 ml of acetone containing 0.1% of 2,6-di-t-butyl-4-hydroxytoluene to precipitate a polymer. After filtration, the polymer recovered was dried in a vacuum dryer at room temperature for 8 hours to obtain 1.1 g of the polymer.

From $^1$H-NMR spectrum analysis, the polymer obtained was confirmed to be a ring-opening metathesis polymer of 2-thia-1,2-dihydrodicyclopentadiene.

Measurement result by 270 MHz $^1$H-NMR; δ(CDCl$_3$): 1.4-3.6 (10H), 5.2-5.6 (2H)

Weight average molecular weight (Mw) of this polymer was 18,000.

This polymer was dissolved in chloroform, and cast on a PET film to prepare a film having a thickness of 100 μm. Refractive index (nd) of this film was 1.590, and Abbe number was 41. Further, light transmittance was 89%.

Example 10

200 ml four-necked flask having a magnetic stirring bar therein was dried with a heat gun under reduced pressure, and was replaced with nitrogen. 1.0 g of a ring-opening metathesis polymer of 2-thia-1,2-dihydrodicyclopentadiene obtained in Example 9 and 45 ml of o-dichlorobenzene were placed in the flask, followed by stirring and dissolving at room temperature. 6.1 g (32.9 mmol) of p-toluenesulfonyl hydrazide and 4.2 g (32.9 mmol) of N,N'-dimethylcyclohexyl amine were added into this solution, and reaction was conducted at 110° C. for 4 hours. After completion of the reaction, the reaction liquid was cooled to room temperature, and poured in 150 ml of methanol to precipitate a polymer. The polymer precipitated was filtered off, and then dissolved in 50 ml of chloroform, and an insoluble content was filtered out. The filtrate was poured in 150 ml of methanol to again precipitate a polymer. After filtration, the polymer recovered was dried in a vacuum dryer at 100° C. for 5 hours to obtain 0.9 g of a polymer. From H-NMR spectrum analysis, the polymer obtained was a hydride of a 2-thia-1,2-dihydro dicyclopentadiene ring-opening metathesis polymer.

Measurement result by 270 MHz $^1$H-NMR; δ(CDCl$_3$): 1.4-3.6 (10H), 5.2-5.6 (2H)

Weight average molecular weight (Mw) of this polymer was 18,000.

This polymer was pressed at 220° C. to prepare a film having a thickness of 100 µm. Light transmittance of this film was 90%, refractive index (nd) was 1.57, and Abbe number was 45.

Example 11

50 ml Schlenik flask having a magnetic stirring bar therein was dried with a heat gun under reduced pressure, and was sufficiently replaced with nitrogen. 7.6 mg (10 µmol) of molybdenum complex represented by the above general formula (11) was placed in the flask. 4.6 ml of dried chloroform and 3.4 mg (25 µmol) of phenylvinyl sulfide were weighed with a syringe and placed in this Schlenik flask to prepare a metathesis polymerization catalyst solution. Next, 0.38 g (2.5 mmol) of 2-thia-1,2-dihydrodicyclopentadiene obtained in Synthesis Example 48 was charged, the flask was immersed in an oil bath adjusted to 60° C., and polymerization was conducted at room temperature for 30 minutes.

The polymerization liquid was poured in 150 ml of acetone containing 0.1% of 2,6-di-t-butyl-4-hydroxytoluene to precipitate a polymer. After filtration, the polymer recovered was dried in a vacuum dryer at room temperature for 8 hours to obtain 0.37 g of the polymer.

From $^1$H-NMR spectrum analysis, the polymer obtained was confirmed to be a ring-opening metathesis polymer of 2-thia-1,2-dihydrodicyclopentadiene.

Measurement result by 270 MHz $^1$H-NMR; $\delta(CDCl_3)$: 1.4-3.6 (10H), 5.2-5.6 (2H)

Weight average molecular weight (Mw) of this polymer was 100,000.

This polymer was dissolved in chloroform, and cast on a PET film to prepare a film having a thickness of 100 µm. Refractive index (nd) of this film was 1.590, and Abbe number was 41. Further, light transmittance was 89%.

Comparative Example 1

20.3 g of a ring-opening metathesis polymer of dicyclopentadiene was obtained by polymerizing in the same manner as in Example 1, except for using 20.5 g of dicyclopentadiene in place of 5.0 g of 1,3-dithiotricyclo-[5,4,0,1$^{6,9}$]-7-deodecene. Weight average molecular weight in terms of polystyrene conversion of this ring-opening metathesis polymer of dicyclopentadiene was 90,000.

Hydrogenation was conducted in the same manner as in Example 2, except for using 20 g of the ring-opening metathesis polymer of dicyclopentadiene in place of 3.5 g of the ring-opening metathesis polymer of 1,3-dithiotricyclo-[5,4,0,1$^{6,9}$]-7-deodecene, thereby obtaining a hydride of the ring-opening metathesis polymer of dicyclopentadiene. Weight average molecular weight of this hydride was 90,000, and glass transition temperature was 95° C.

The polymer obtained was dissolved in chloroform, and a film having a thickness of 100 µm was prepared by a casting method.

Light transmittance of the film was 90%, refractive index (nd) was 1.531, and Abbe number was 58.

Comparative Example 2

Commercially available polystyrene (weight average molecular weight is 190,000, and glass transition temperature is 87° C.) was dissolved in chloroform, and a film having a thickness of 100 µm was prepared by a casting method.

Light transmittance of the film was 88%, refractive index (nd) was 1.591, and Abbe number was 31.

Comparative Example 3

Commercially available polycarbonate (weight average molecular weight is 190,000, and glass transition temperature is 147° C.) was dissolved in methylene chloride, and a film having a thickness of 100 µm was prepared by a casting method.

Light transmittance of the film was 89%, refractive index (nd) was 1.584, and Abbe number was 31.

Comparative Example 4

Commercially available acrylonitrile-styrene copolymer (weight average molecular weight is 130,000, glass transition temperature is 106° C., and acrylonitrile content is 29 wt %) was dissolved in methylene chloride, and a film having a thickness of 100 µm was prepared by a casting method.

Light transmittance of the film was 90%, refractive index (nd) was 1.564, and Abbe number was 35.

While the present invention has been described in detail and with reference to specific embodiments thereof, it will be apparent to one skilled in the art that various changes and modifications can be made therein without departing from the spirit and scope thereof.

This application is based on Japanese Patent Application No. 2005-150639 filed May 24, 2005, Japanese Patent Application No. 2005-150640 filed May 24, 2005, Japanese Patent Application No. 2005-162287 filed Jun. 2, 2005 and Japanese Patent Application No. 2006-071438 filed Mar. 15, 2006, the entire contents thereof being hereby incorporated by reference.

INDUSTRIAL APPLICABILITY

The sulfur-containing cyclic olefin resin of the present invention has high transparency and high refractive index, and is useful as a raw material of various plastic lenses, prism sheets and the like. Therefore, industrial value of the present invention is remarkable.

The invention claimed is:

1. A sulfur-containing cyclic olefin resin, characterized by comprising a unit represented by the following general formula (1) and having a weight average molecular weight of from 1,000 to 1,000,000,

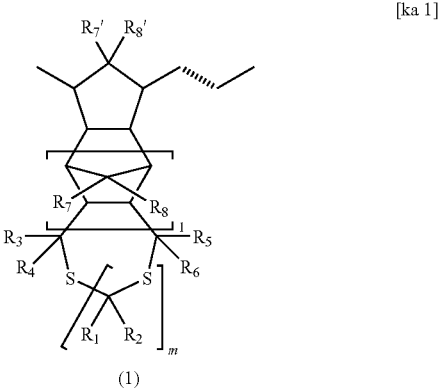

[ka 1]

(1)

wherein $R_1$ to $R_6$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms or a heterocyclic compound, further $R_3$ to $R_6$ may be a halogen atom, $R_3$ and $R_4$, and $R_5$ and $R_6$ may form a ring containing carbon, oxygen, sulfur or nitrogen, $R_7$, $R_{7'}$, $R_8$ and $R_{8'}$ each independently represents a hydrogen atom or a methyl group, . . . represents a single bond or a double bond, and l and m each is 0 or 1.

2. The sulfur-containing cyclic olefin resin as claimed in claim 1, characterized by comprising a unit represented by the following general formula (2) wherein all of $R_3$ to $R_8$, $R_{7'}$, and $R_{8'}$ are a hydrogen atom and m is 1 in the general formula (1), and having a weight average molecular weight of from 1,000 to 1,000,000,

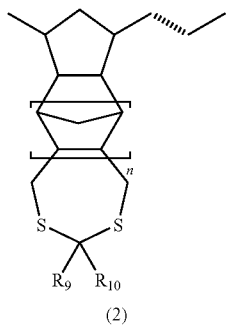

(2)

wherein $R_9$ and $R_{10}$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms or a heterocyclic compound, . . . represents a single bond or a double bond, and n is 0 or 1.

3. The sulfur-containing cyclic olefin resin as claimed in claim 1, characterized by comprising a unit represented by the following general formula (3) wherein all of $R_7$, $R_8$, $R_{7'}$ and $R_{8'}$ are a hydrogen atom and m is 0 in the general formula (1), and having a weight average molecular weight of from 1,000 to 1,000,000,

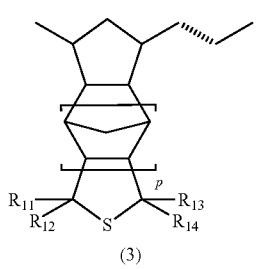

(3)

wherein $R_{11}$ to $R_{14}$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms, a heterocyclic compound or a halogen group, $R_{11}$ and $R_{12}$, and $R_{13}$ and $R_{14}$ may form a ring containing carbon, oxygen, sulfur or nitrogen, . . . represents a single bond or a double bond, and p is 0 or 1.

4. The sulfur-containing cyclic olefin resin as claimed in claim 1, characterized by comprising a unit wherein all of $R_1$ to $R_6$, $R_{7'}$ and $R_{8'}$ are a hydrogen atom, m is 1, and l is 0 in the general formula (1), and having a weight average molecular weight of from 1,000 to 1,000,000.

5. The sulfur-containing cyclic olefin resin as claimed in claim 1, characterized by comprising a unit wherein all of $R_3$ to $R_6$, $R_{7'}$ and $R_{8'}$ are a hydrogen atom and m and l are 0 in the general formula (1), and having a weight average molecular weight of from 1,000 to 1,000,000.

6. A method of producing a sulfur-containing cyclic olefin resin comprising a unit represented by the following formula (1) and having a weight average molecular weight of from 1,000 to 1,000,000, characterized by subjecting a sulfur-containing cyclic compound represented by the following general formula (4) to metathesis polymerization,

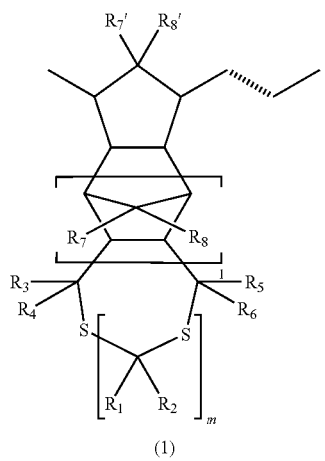

(1)

wherein $R_1$ to $R_6$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms or a heterocyclic compound, further $R_3$ to $R_6$ may be a halogen atom, $R_3$ and $R_4$, and $R_5$ and $R_6$ may form a ring containing carbon, oxygen, sulfur or nitrogen, $R_7$, $R_{7'}$, $R_8$ and $R_{8'}$ each independently represents a hydrogen atom or a methyl group, . . . represents a single bond or a double bond, and l and m each is 0 or 1,

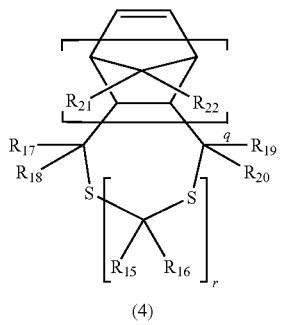

(4)

wherein $R_{15}$ to $R_{20}$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms or a heterocyclic compound, further $R_{17}$ to $R_{20}$ may be a halogen atom, $R_{17}$ and $R_{18}$, and $R_{19}$ and $R_{20}$ may form a ring containing carbon, oxygen, sulfur or nitrogen, $R_{21}$ and $R_{22}$ each independently represents a hydrogen atom or a methyl group, q is 1 or 2, and r is 0 or 1.

7. The method of producing a sulfur-containing cyclic olefin resin as claimed in claim 6, characterized in that hydrogenation is conducted after metathesis polymerization of the sulfur-containing cyclic compound represented by the general formula (4).

8. The method of producing a sulfur-containing cyclic olefin resin as claimed in claim 6, characterized in that the sulfur-containing cyclic compound represented by the general formula (5) wherein all of $R_{17}$ to $R_{22}$ are a hydrogen atom and r is 1 in the general formula (4) is subjected to metathesis polymerization,

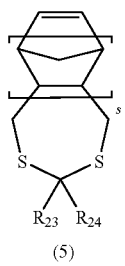

(5)

wherein $R_{23}$ and $R_{24}$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms or a heterocyclic compound, and s is 1 or 2.

9. The method of producing a sulfur-containing cyclic olefin resin as claimed in claim 8, characterized in that hydrogenation is conducted after metathesis polymerization of the sulfur-containing cyclic compound represented by the general formula (5).

10. The method of producing a sulfur-containing cyclic olefin resin as claimed in claim 6, characterized in that the sulfur-containing cyclic compound represented by the general formula (6) wherein $R_{21}$ and $R_{22}$ are a hydrogen atom and r is 0 in the general formula (4) is subjected to metathesis polymerization,

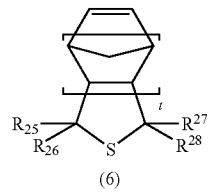

(6)

wherein $R_{25}$ to $R_{28}$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms, a heterocyclic compound or a halogen group, $R_{25}$ and $R_{26}$, and $R_{27}$ and $R_{28}$ may form a ring containing carbon, oxygen, sulfur or nitrogen, and t is 1 or 2.

11. The method of producing a sulfur-containing cyclic olefin resin as claimed in claim 10, characterized in that hydrogenation is conducted after metathesis polymerization of the sulfur-containing cyclic compound represented by the general formula (6).

12. An optical material, characterized by comprising a sulfur-containing cyclic olefin resin comprising a unit represented by the following general formula (1) and having a weight average molecular weight of from 1,000 to 1,000,000,

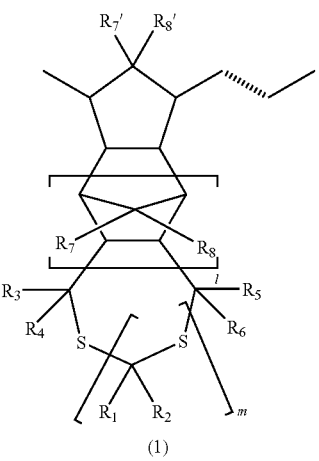

(1)

wherein $R_1$ to $R_6$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms or a heterocyclic compound, further $R_3$ to $R_6$ may be a halogen atom, $R_3$ and $R_4$, and $R_5$ and $R_6$ may form a ring containing carbon, oxygen, sulfur or nitrogen, $R_7$, $R_{7'}$, $R_8$ and $R_{8'}$ each independently represents a hydrogen atom or a methyl group, . . . represents a single bond or a double bond, and l and m each is 0 or 1.

13. A lens, characterized by comprising a sulfur-containing cyclic olefin resin comprising a unit represented by the following general formula (1) and having a weight average molecular weight of from 1,000 to 1,000,000,

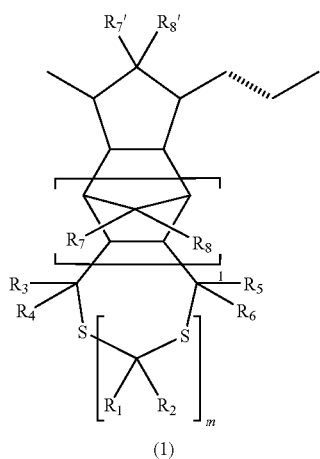

(1)

wherein $R_1$ to $R_6$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms or a heterocyclic compound, further $R_3$ to $R_6$ may be a halogen atom, $R_3$ and $R_4$, and $R_5$ and $R_6$ may form a ring containing carbon, oxygen, sulfur or nitrogen, $R_7$, $R_{7'}$, $R_8$ and $R_{8'}$ each independently represents a hydrogen atom or a methyl group, . . . represents a single bond or a double bond, and l and m each is 0 or 1.

14. A condensing lens, characterized by comprising a sulfur-containing cyclic olefin resin comprising a unit represented by the following general formula (1) and having a weight average molecular weight of from 1,000 to 1,000,000,

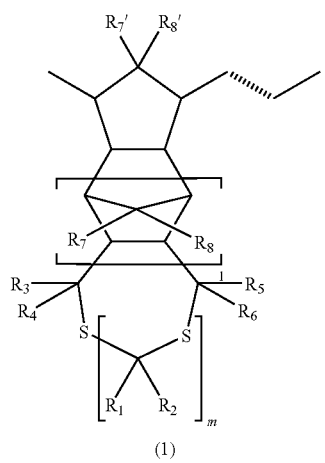

(1)

wherein $R_1$ to $R_6$ each independently represents a hydrogen atom, an alkyl group having from 1 to 20 carbon atoms, an aralkyl group having from 1 to 20 carbon atoms, an aromatic group having from 1 to 20 carbon atoms, a cyano group, an alkoxy group having from 1 to 10 carbon atoms or a heterocyclic compound, further $R_3$ to $R_6$ may be a halogen atom, $R_3$ and $R_4$, and $R_5$ and $R_6$ may form a ring containing carbon, oxygen, sulfur or nitrogen, $R_7$, $R_{7'}$, $R_8$ and $R_{8'}$ each independently represents a hydrogen atom or a methyl group, . . . represents a single bond or a double bond, and 1 m each is 0 or 1.

* * * * *